United States Patent [19]

Julius et al.

[11] Patent Number: 4,985,352
[45] Date of Patent: Jan. 15, 1991

[54] DNA ENCODING SEROTONIN 1C (5HT1C) RECEPTOR, ISOLATED 5HT1C RECEPTOR, MAMMALIAN CELLS EXPRESSING SAME AND USES THEREOF

[75] Inventors: David J. Julius; Richard Axel; Thomas M. Jessell, all of New York, N.Y.

[73] Assignee: The Trustees of Columbia University in the City of New York, New York, N.Y.

[21] Appl. No.: 298,639

[22] Filed: Jan. 18, 1989

Related U.S. Application Data

[63] Continuation-in-part of Ser. No. 162,654, Feb. 29, 1988, abandoned.

[51] Int. Cl.$^5$ .................. C12Q 1/68; C12M 15/00; G01N 33/566; C07H 15/12
[52] U.S. Cl. ................................ 435/6; 435/172.1; 435/240.2; 435/272; 435/320; 436/501; 536/26; 536/27; 536/28; 935/18; 935/23; 935/32; 935/33; 935/34; 935/56; 935/60; 935/70; 935/77; 935/78; 935/80
[58] Field of Search ............... 435/6, 172.1, 240.2, 435/272, 320; 436/501; 536/26-28; 935/18, 23, 32, 33, 34, 56, 60, 70, 77, 78, 80

[56] References Cited

PUBLICATIONS

Andrade, R. and Nicoll, R. A., *Journal of Physiology*, vol. 394, pp. 99–124 (1987).
Andrade, R. et al., *Science*, vol. 234, pp. 1261–1265 (1986).
Chung, F. Z. et al., *Journal of Biological Chemistry*, vol. 263, pp. 4052–4055 (1988).
Conn, P. J. et al., *Proc. Natl. Acad. Sci. U.S.A.*, vol. 83, pp. 4086–4088 (1986).
de Chaffoy de Courcelles, D. et al., *Journal of Biological Chemistry*, vol. 260, pp. 7603–7608 (1985).
Dixon, R. A. F. et al., *EMBO Journal*, vol. 6, pp. 3269–3275 (1987).
Dixon, R. A. F. et al., *Nature*, vol. 326, pp. 73–77 (1987).
Dohlman, H. G. et al., *Biochemistry*, vol. 27, pp. 1813–1817 (1988).
Dohlman, H. G. et al., *Biochemistry*, vol. 26, pp. 2657–2664 (1987).
Gundersen, C. B. et al., *Proc. R. Soc. London*, Series B, vol. 219, pp. 103–109 (1983).
Kadan, M. J. et al., *Journal of Neurochemistry*, vol. 43, pp. 601–606 (1984).
Lubbert, H. et al., *Proc. Natl. Acad. Sci. U.S.A.*, vol. 84, pp. 4332–4336 (1987).
Lubbert, H., *Journal of Neuroscience*, vol. 7, pp. 1159–1165 (1987).
Maddon, P. J. et al., *Cell*, vol. 47, pp. 333–348 (1986).
Masu, Y. et al., *Nature*, vol. 329, pp. 836–838 (1987).
Pazos, A. and Palacios, J. M., *Brain Research*, vol. 346, pp. 205–230 (1985).
Peroutka, S. J., *Ann. Rev. Neurosci.*, vol. 11, pp. 45–60 (1988).
Sibley, D. R. et al., *Cell*, vol. 48, pp. 913–922 (1987).
Siegelbaum, S. A. et al., *Nature*, vol. 299, pp. 413–417 (1982).
Strader, C. D. et al., *Proc. Natl. Acad. Sci. U.S.A.*, vol. 84, pp. 4384–4388 (1987).
Strader, C. D. et al., *Journal of Biological Chemistry*, vol. 262, pp. 16439–16443 (1987).
Sumikawa, K. et al., *Proc. R. Soc. London*, Series B, vol. 223, pp. 255–260 (1984).
Takahashi, T. et al., *Proc. Natl. Acad. Sci. U.S.A.*, vol. 84, pp. 5063–5067 (1987).
Yagaloff, K. A. and Hartig, P. R., *Journal of Neuroscience*, vol. 5, pp. 3178–3183 (1985).

*Primary Examiner*—Jack Spiegel
*Attorney, Agent, or Firm*—John P. White

[57] ABSTRACT

The invention relates to DNA encoding a functional serotonin 5HT1c receptor, e.g., cDNA, and to the isolated, functional serotonin 5HT1c receptor encoded by such DNA. The invention also relates to mammalian cells expressing the cDNA encoding the 5HT1c receptor and to a DNA probe useful for detecting nucleic acid encoding the serotonin 5HT1c receptor. This invention provides methods for determining binding to the serotonin 5HT1c receptor, methods of detecting the expression, and the presence of the serotonin 5HT1c receptor on the surface of a cell and to a method of screening drugs to identify drugs which specifically interact with, and bind to the serotonin 5HT1c receptor on the surface of a cell.

17 Claims, 30 Drawing Sheets

Figure 1

```
-687 GGGGCTCTGGTGCTCACTGAGGAAGCTTCCTTAGTGTACCGATCTTAATGATTGAGCC
-628 CTTGGAGCAGCAAGATTGTTAATCTTGTTGCTCCTTTGGCCTGTCTATCCCTTACCTT
-569 CCTATTACATATGAACTTTCTCGTTCTGCACATCGATTGTCGTCGGGTCGTGAGA
-510 TCGTCGTGGTGCTCCGTGGTGTCTTCGTCCGCTTAGAATAGTGTAGTTAGTTAGGG
-451 CCTTCAAAGAAGAAAGAAGAACGATTGGGCCGGAGAGATGCTGGAGGTGTCAGTTCT
-392 ATGCTAGAGTAGGGTAGTGAAACAATCCCAGCCAAACCTTTCCGGGGGGCAGGTTG
-333 CCCACAGAGGTCGACTTGCCGCGCGTCCTTCGCGCACGCTCCCTCCATCCTTCTT
-274 TCCGTCTGCTGAGACGCAAGGTTGCGGCGCACGCTGAGCACGCACTGACTGCCGCG
-214 GGCTCCGCTGGGCGATTGCAGCCGAGTCCGTTTCTGTCTAGCTGCCGCCGGGCGACC
-155 TGCCTGGTCTTCCTCCCGACGCTAGCGGGTTGTCAACTATTACCTGCAAGCATAGCC
-96  AACGAACACCTTCTTTCCAAATTAATTGGAATGAAACAATTCTGTTAACTTCCTAATTC
-37  TCAGTTTGAAACTCTGGTTGCTTAAGCCTGAAGCAATC

1 ATG GTG AAC CTT GGC AAC GCG GTG CGC TCG CTC CTG ATG CAC CTA
    Met Val Asn Leu Gly Asn Ala Val Arg Ser Leu Leu Met His Leu

46 ATC GGC CTA TTG GTT TGG CAA TTC GAT ATT TCC ATA AGT CCA GTA
    Ile Gly Leu Val Trp Gln Phe Asp Ile Ser Ile Ser Pro Val
```

Figure 1
(continued)

```
 91 GCA GCT ATA GTA ACT GAC ACT TTT AAT TCC TCC GAT GGT GGA CGC
    Ala Ala Ile Val Thr Asp Thr Phe Asn Ser Ser Asp Gly Gly Arg

136 TTG TTT CAA TTC CCG GAC GGG GTA CAA AAC TGG CCA GCA CTT TCA
    Leu Phe Gln Phe Pro Asp Gly Val Gln Asn Trp Pro Ala Leu Ser

181 ATC GTC GTG ATT ATA ATC ATG ACA ATA GGG GGC AAC ATT CTT GTT
    Ile Val Val Ile Ile Ile Met Thr Ile Gly Gly Asn Ile Leu Val

226 ATC ATG GCA GTA AGC ATG GAG AAG CTG CAC AAT GCA ACC AAT
    Ile Met Ala Val Ser Met Glu Lys Leu His Asn Ala Thr Asn

271 TAC TTC TTA ATG TCC CTA GCC ATT GCT GAT ATG CTG GTG GGA CTA
    Tyr Phe Leu Met Ser Leu Ala Ile Ala Asp Met Leu Val Gly Leu

316 CTT GTC ATG CCC CTG TCC CTG CTT GCT ATT CTT TAT GAT TAT GTC
    Leu Val Met Pro Leu Ser Leu Leu Ala Ile Leu Tyr Asp Tyr Val
```

Figure 1
(continued)

```
361 TGG CCT TTA CCT AGA TAT TTG TGC CCC GTC TGG ATT TCA CTA GAT
    Trp Pro Leu Pro Arg Tyr Leu Cys Pro Val Trp Ile Ser Leu Asp

406 GTG CTA TTT TCA ACT GCG TCC ATC ATG CAC CTC TGC GCC ATA TCG
    Val Leu Phe Ser Thr Ala Ser Ile Met His Leu Cys Ala Ile Ser

451 CTG GAC CGG TAT GTA GCA ATA CGT AAT CCT ATT GAG CAT AGC CGG
    Leu Asp Arg Tyr Val Ala Ile Arg Asn Pro Ile Glu His Ser Arg

496 TTC AAT TCG CGG ACT AAG GCC ATC ATG AAG ATT GCC ATC GTT TGG
    Phe Asn Ser Arg Thr Lys Ala Ile Met Lys Ile Ala Ile Val Trp

541 GCA ATA TCA ATA GGA GTT TCA GTT CCT ATC CCT GTG ATT GGA CTG
    Ala Ile Ser Ile Gly Val Ser Val Pro Ile Pro Val Ile Gly Leu

586 AGG GAC GAA AGC AAA GTG TTC GTG AAT AAC ACC ACG TGC GTG CTC
    Arg Asp Glu Ser Lys Val Phe Val Asn Asn Thr Thr Cys Val Leu
```

Figure 1
(continued)

```
631 AAT GAC CCC AAC TTC GTT CTC ATC GGG TCC TTC GTG GCA TTC TTC
    Asn Asp Pro Asn Phe Val Leu Ile Gly Ser Phe Val Ala Phe Phe

676 ATC CCG TTG ACG ATT ATG GTG ATC ACC TAC TTC TTA ACG ATC TAC
    Ile Pro Leu Thr Ile Met Val Ile Thr Tyr Phe Leu Thr Ile Tyr

721 GTC CTG CGC CGT CAA ACT CTG ATG TTA CTT CGA GGT CAC ACC GAG
    Val Leu Arg Arg Gln Thr Leu Met Leu Leu Arg Gly His Thr Glu

766 GAG GAA CTG GCT AAT ATG AGC CTG AAC TTT CTG AAC TGC TGC TGC
    Glu Glu Leu Ala Asn Met Ser Leu Asn Phe Leu Asn Cys Cys Cys

811 AAG AAG AAT GGT GGT GAG GAA GAG AAC GCT CCG AAC CCT AAT CCA
    Lys Lys Asn Gly Gly Glu Glu Glu Asn Ala Pro Asn Pro Asn Pro

856 GAT CAG AAA CCA CGT CGA AAG AAA GAA AAG CGT CCC AGA GGC
    Asp Gln Lys Pro Arg Arg Lys Lys Glu Lys Arg Pro Arg Gly
```

Figure 1
(continued)

```
901  ACC ATG CAA GCT ATC AAC AAC GAA AAG AAA GCT TCC AAA GTC CTT
     Thr Met Gln Ala Ile Asn Asn Glu Lys Lys Ala Ser Lys Val Leu

946  GGC ATT GTA TTC TTT GTG TTT CTG ATC ATG TGG TGC CCG TTT TTC
     Gly Ile Val Phe Phe Val Phe Leu Ile Met Trp Cys Pro Phe Phe

991  ATC ACC AAT ATC CTG TCG GTT CTT TGT GGG AAG GCC TGT AAC CAA
     Ile Thr Asn Ile Leu Ser Val Leu Cys Gly Lys Ala Cys Asn Gln

1036 AAG CTA ATG GAG AAG CTT CTC AAT GTG TTT GTG TGG ATT GGC TAT
     Lys Leu Met Glu Lys Leu Leu Asn Val Phe Val Trp Ile Gly Tyr

1081 GTG TGT TCA GGC ATC AAT CCT CTG GTG TAC ACT CTC TTT AAT AAA
     Val Cys Ser Gly Ile Asn Pro Leu Val Tyr Thr Leu Phe Asn Lys

1126 ATT TAC CGA AGG GCT TTC TCT AAA TAT TTG CGC TGC GAT TAT AAG
     Ile Tyr Arg Arg Ala Phe Ser Lys Tyr Leu Arg Cys Asp Tyr Lys
```

Figure 1
(continued)

```
1171 CCA GAC AAA AAG CCT CCT GTT CGA CAG ATT CCT AGG GTT GCT GCC
     Pro Asp Lys Lys Pro Pro Val Arg Gln Ile Pro Arg Val Ala Ala

1216 ACT GCT TTG TCT GGG AGG GAG CTC AAT GTT AAC ATT TAT CGG CAT
     Thr Ala Leu Ser Gly Arg Glu Leu Asn Val Asn Ile Tyr Arg His

1261 ACC AAT GAA CGT GTG GCT AGG AAA GCT AAT GAC CCT GAG CCT GGC
     Thr Asn Glu Arg Val Ala Arg Lys Ala Asn Asp Pro Glu Pro Gly

1306 ATA GAG ATG CAG GTG GAG AAC TTA GAG CTG CCA GTC AAC CCC TCT
     Ile Glu Met Gln Val Glu Asn Leu Glu Leu Pro Val Asn Pro Ser

1351 AAT GTG GTC AGC GAG AGG ATT AGT AGT GTG TAA ---
     Asn Val Val Ser Glu Arg Ile Ser Ser Val ---

1384 GCGAAGAGCAGGCAGACTTCCTACAGGAAAGTTCTGTAGGAAAGTCCTCCCCACCCC
1443 CCGTGATTTCCTGTGAATCATAACTAATCATAATGTAAATATTGCTGTGACAAGACAGTGTT
1502 TTTATAAATAGCTTTGCAACCCTGTACTTTACATCATCATGCGTTAATAGTGAGATTCGGG
```

Figure 2

Table Of Codon Usage In 5HTIC.DNA
As Translated Above

| | | | | | | | | | | | | |
|---|---|---|---|---|---|---|---|---|---|---|---|---|
| TTT | Phe | 9 | 2.0% | TCT | Ser | 3 | 0.7% | TAT | Tyr | 8 | 1.7% | TGT | Cys | 3 | 0.7% |
| TTC | Phe | 13 | 2.8% | TCC | Ser | 8 | 1.7% | TAC | Tyr | 5 | 1.1% | TGC | Cys | 8 | 1.7% |
| TTA | Leu | 5 | 1.1% | TCA | Ser | 6 | 1.3% | TAA | --- | --- | --- | TGA | --- | 0 | --- |
| TTG | Leu | 6 | 1.3% | TCG | Ser | 4 | 0.9% | TAG | --- | --- | --- | TGG | Trp | 7 | 1.5% |
| | | | | | | | | | | | | |
| CTT | Leu | 10 | 2.2% | CCT | Pro | 12 | 2.6% | CAT | His | 2 | 0.4% | CGT | Arg | 5 | 1.1% |
| CTC | Leu | 7 | 1.5% | CCC | Pro | 5 | 1.1% | CAC | His | 4 | 0.9% | CGC | Arg | 4 | 0.9% |
| CTA | Leu | 7 | 1.5% | CCA | Pro | 6 | 1.3% | CAA | Gln | 6 | 1.3% | CGA | Arg | 4 | 0.9% |
| CTG | Leu | 16 | 3.5% | CCG | Pro | 4 | 0.9% | CAG | Gln | 3 | 0.7% | CGG | Arg | 4 | 0.9% |
| | | | | | | | | | | | | |
| ATT | Ile | 16 | 3.5% | ACT | Thr | 7 | 1.5% | AAT | Asn | 18 | 3.9% | AGT | Ser | 3 | 0.7% |
| ATC | Ile | 17 | 3.7% | ACC | Thr | 7 | 1.5% | AAC | Asn | 16 | 3.5% | AGC | Ser | 5 | 1.1% |
| ATA | Ile | 9 | 2.0% | ACA | Thr | 1 | 0.2% | AAA | Lys | 10 | 2.2% | AGA | Arg | 2 | 0.4% |
| ATG | Met | 17 | 3.7% | ACG | Thr | 3 | 0.7% | AAG | Lys | 14 | 3.0% | AGG | Arg | 6 | 1.3% |
| | | | | | | | | | | | | |
| GTT | Val | 10 | 2.2% | GCT | Ala | 11 | 2.4% | GAT | Asp | 7 | 1.5% | GGT | Gly | 5 | 1.1% |
| GTC | Val | 8 | 1.7% | GCC | Ala | 6 | 1.3% | GAC | Asp | 7 | 1.5% | GGC | Gly | 8 | 1.7% |
| GTA | Val | 6 | 1.3% | GCA | Ala | 7 | 1.5% | GAA | Glu | 6 | 1.3% | GGA | Gly | 4 | 0.9% |
| GTG | Val | 20 | 4.3% | GCG | Ala | 2 | 0.4% | GAG | Glu | 13 | 2.8% | GGG | Gly | 5 | 1.1% |

Number of identified codons = 460
Number of unidentified codons = 0
Approximate Molecular Weight = 51898.80

5-HT receptor cDNA

Figure 11

```
RAT  5HT    MVN------------LGNAVRSLLMHLIGLLVWQFDISISPVA
HAM  BAR    MGP------------PGNDSDFLLTTNGSHV------------
BOV  SK     MGA------------CVVMTDI---NISSG-------------
HUM  A2AR   MGSLQPD--------AGNASWNGTEAPGGGA------------
RAT  M3     EAGLPLGTVTQL---GSYNISQETGNFSSND------------
BOV  RHOD   -----MNGTEGP---NFYVPFSNKTGVVRSP------------
```

Figure 11
(continued)

```
RAT 5HT     GIVTDTFNSSDGGRLFQFPDGVQNWPALSIVVIIIMTI--GGNILVIMAVSMEKKLHNA
HAM BAR     ----PDHDVTEERDEAWVVGMAILMSVIVLAIVF---GNLVITAIAKFERLQTV
BOV SK      ----LDSNATGITAFSMPGWQLALWTAAYLALVLVAVMGNATVIWILAHQRMRTV
HUM A2AR    ----RATPYSLQVTLTLVCLAGLLM----LLTVF---GNVLVIAVFTSRALKAP
RAT M3      ----TSSDPLGGHTIWQVFIAFLTGFLALVTII---GNILVIVAFKVNKQLKTV
BOV RHOD    ----FEAPQYYLAEPWQFSMLAAYMFLLIMLGFP---INFLTLYVTVQHKKLRTP
```

```
                                                              IV
RAT 5HT    DRY V A I RNP I EHSRFNSRTKA M K I A I VWA I S I GVSV-P I P V GLRDESKVFVNNTTC
HAM BAR    DRY V A I TSP F KYQSLLTKNK A R M QV I LMVW I VS GLTSF L P---Q MHWYRATHQKA I DC
BOV SK     DRY M A I VHF F--QPRLSAPGTRA K M GV WI VALALAF-P I---Q CFYSTITTDEGATKC
HUM A2AR   DRY WS I TQA I EYNLKRTPRRIKA I T MVW I V S AVIS FPP L IS EKKGGGGGPQPAEPR
RAT M3     DRY F S L TR P L TYRAKRTTKRRGVM I GL AW V I S FVLWA-P A I LFWQYFVGKRTVPPGE
BOV RHOD   ERY V V VCKP M SNFRFGENH-A I M GVA F TW VMALACAAP P---L VGWSRVIPEGMQCSC
```

Figure 11
(continued)

```
RAT  5HT    VL------NDPN N FVL- I G S FV A -F F I -PL T L MV I T V F-LTIY V L R RQT  ----(39)
HAM  BAR    YHKETCCDFFTN N QAYAL A S SIVS F YV -PL V VM YF VYSR-VFQ V A K RQL  ----(25)
BOV  SK     VVAWPEDSGGKM--LLYHLIV I A L IYF L PL V VM F FVAYSVIGLTLW R RSV
HUM  A2AR   CEINDQ------KWYV I S S CIGS F F A -P C L I M ILVYVRIYQIAK R R TR  ----(125)
RAT  M3     FIQFLSE-----PTITFGTAI A A F YM -PL V T L M T ILVWRIVKETE R R TK  ----(207)
BOV  RHOD   GIDYVTPHEETN N ESFV I YMFVVH F I I -PL I V IFFC Y GQLVFT V KEAAA
                                           V
```

Figure 11
(continued)

```
                                                              VI
RAT 5HT    DQKPRRKKKEKRPRGTMQAINN-EKKASKVLGIVFFVFLIMWCPFFITNILSVLCGKAC
HAM BAR    HGL-RRSSKFCL---------KEIKALKTLGIIMGTFTLCWLPFFIVNIVHVIQDNLI
BOV SK     PGHQAHGANLRH---------------------LGIIMGTFTLCWLPFFIVNIVHVIQDNLI
HUM A2AR   SGLPRRRAGAGG---------IQAKRKFVKTMVLVVTFAICWLPYHLYFLGTFQEDIY
RAT M3     TRSQITKRKRM----------QNREKRFTFVLAVVIGVFVVCWFPFFTYTTAVGCSV-
BOV RHOD   QQ-QES---------------SLIKEKKAAQTLSAILLAFLITWTPYNIMVLVNTFCDSCI
           ATTQKAEKEVTRMVIMVIAFLICWLPYAGVAFYIFTHQGSD
```

Figure 11
(continued)

```
                            VII
RAT  SHT   -NQK----LMEK L L N F VW I GY V C SG - I N P L VV T L F N K I YR R A F SK Y L R D Y K P D K K P P V R Q
HAM  BAR   -PKE----VVIL L N - - -W L GY V N SA - F N P L I VC R S - P D F R I A F Q E L L C L R R S S K A Y G N G Y
BOV  SK    -CHKFIQQVYLAL F - - -W L AM S S TM - Y N P T I VC C L N H R F R S G F R L A F R C P W V T P T E E D KM
HUM  A2AR  -PRT----FKFF W F G Y C N S S - L N P V I Y T I F N H D F R R A F K K I C R G D R K R I V
RAT  M3    -PKT----YWN L GY - - -W L C Y I N S T - V N P V C Y A L C N K T F R T T E K T L L C Q C D K R K Q Q Y
BOV  RHOD  -FGP----IFMTIP - - -A F F A K T S A V Y N P V I Y I MM N K Q F R N C M V T T L C G K N P L G D D E A S T
```

Figure 11
(continued)

```
RAT 5HT    IPRVAATALSGRELNVNIYRHTNERVARKANDPEPGIEMQVENLELPVNPSNVVSERISS
HAM BAR    SSNSNGKTDYMGEASGCQLGQEKESERLCEDPPGTESFVNCQCTVPSLSLDSQGKNCSTN
BOV SK     ELTYTPSLSTRVNRCHTKEIFFMSGDVAPSEAVNGQAESPQAGVSTEP
HUM A2AR
RAT M3     QQRQSVIFHKRVPEQAL
BOV RHOD   TVSKTETSQVAPA
```

DNA ENCODING SEROTONIN 1C (5HT1C) RECEPTOR, ISOLATED 5HT1C RECEPTOR, MAMMALIAN CELLS EXPRESSING SAME AND USES THEREOF

This application is a continuation-in-part of U.S. Ser. No. 162,654, filed Feb. 29, 1988, now abandoned, the contents of which are hereby incorporated by reference.

BACKGROUND OF THE INVENTION

Throughout this application various publications are referenced by Arabic numerals within parentheses. Full citations for these references may be found at the end of the specification immediately preceding the claims. The disclosures of these publications in their entireties are hereby incorporated by reference in this application in order to more fully describe the state of the art to which this invention pertains.

Serotonin, 5-hydroxytryptamine (5HT), is a biogenic amine that functions as a neurotransmitter (12), a hormone (13), and a mitogen (14). Serotonin modulates many forms of synaptic transmission and is believed to exert a number of effects on the growth of neurons in early development. In the spinal cord, serotonin is involved in the inhibitory control of sensory input and in the facilitation of motor output (15, 16). In the cortex, transmission at serotonergic synapses contributes to affective and perceptual states, and these synapses represent a major site of action of psychotropic drugs such as LSD (17). Serotonergic neurons project to diffuse regions of the brain and exert their physiological effects by binding to cell surface receptors. To date, six serotonin receptor subtypes (5HT1a-1d, 2 and 3) (previously designated 5HT-1A-1D, 2 and 3) have been defined on the basis of their pharmacological properties (18).

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success.

Similarly, the biochemical mechanisms by which these receptors transduce signals across the cell surface have been difficult to ascertain without having welldefined cell populations which express exclusively one receptor sub-type. Serotonin receptor subtypes couple to different intracellular second messenger signaling systems, including the regulation of adenylate cyclase activity (5HT1a and 5HT1b) (19, 20, 21) and phospholipase C activities (5HT1c and 5HT2) (22, 23). The activation of these second messenger pathways by serotonin modulates the excitable properties of both central and peripheral neurons (24, 25, 26, 27). Serotonin receptors are also thought to be linked to the direct modification of ion channel states, and are implicated in mechanisms associated with pain, migraine headaches, and motor control. Moreover, drugs which bind to the serotonin receptor may be useful in treating depression. One difficulty which this involves is the prior difficulty in examining a specific interaction of a drug with the serotonin 5HT1c receptor alone.

The methods provided by this invention provide a simple and qualitative assay to assess this interaction and eliminate the lack of specificity associated with the prior art use of tissue preparations as a semi-defined source of serotonin receptors. The expression of functional receptors in Xenopus oocytes has provided a sensitive assay for detection of mRNA encoding serotonin receptors, in particular the 5HT1c receptor, that couples via inositol phospholipid signaling systems (5, 6, 28). This invention differs from the closest prior art in that NIH 3T3-SR cells can be obtained in any quantity desired, and provides the investigator with a source of receptors which is consistent in its molecular characteristics. Furthermore, this cell line also provides the investigator with a cellular environment in which ligand-receptor interactions can be measured using a simple spectrofluorimetric assay.

Although it has recently been reported that a cDNA fragment encoding the serotonin 5HT1c receptor has been cloned, this fragment does not encode and is not useful in producing functional serotonin 5HT1c receptors. The cDNA clone encodes only the carboxyl-terminal portion of the 5HT1c receptor and was isolated by hybrid-depletion of choroid plexus mRNA coupled with oocyte expression (29). Applicants, in the present invention, have combined cloning in RNA expression vectors with an electrophysiological assay in oocytes to isolate and characterize the expression of a functional cDNA clone encoding the entire 5HT1c receptor.

SUMMARY OF THE INVENTION

The present invention provides DNA encoding a functional serotonin 5HT1c receptor.

The invention also provides a plasmid comprising the DNA encoding a functional serotonin 5HT1c receptor which is designated pSR-1c and deposited under ATCC Accession No. 67636.

Additionally, the present invention provides a plasmid adapted for expression in a mammalian cell which comprises the cDNA encoding a functional serotonin 5HT1c receptor and the regulatory elements necessary for expression of the cDNA in the mammalian cell.

The present invention further provides the transfected NIH3T3 cell designated SR3T3 and deposited under ATCC Accession No. CRL 9651.

In addition, the invention provides a DNA probe useful for detecting nucleic acid encoding the serotonin 5HT1c receptor comprising a nucleic acid molecule of at least about 15 nucleotides having a sequence complementary to a sequence included within the sequence shown in FIG. 1.

The invention herein also concerns an antibody directed to the serotonin 5HT1c receptor.

This invention additionally concerns a monoclonal antibody directed to an epitope of the serotonin 5HT1c receptor present on the surface of a cell and having an amino acid sequence included within the amino acid sequence shown in FIG. 1.

BRIEF DESCRIPTION OF THE FIGURES

FIG. 2. Table of codon usage in 5HT1c DNA.

A. Choroid plexus total RNA was fractionated by sucrose gradient sedimentation to enrich for serotonin receptor mRNA. 50 μg of choroid plexus total RNA was centrifuged through a 5%–25% (w/v) sucrose gradient as described in Experimental details. Collected fractions were assayed for absorbance at 260 nm (o-o) and for serotonin receptor activity by voltage clamp analysis. Fraction 1 corresponds to the top of the gradient (smaller RNA's), and fraction 25 to the bottom (larger RNA's). Positive fractions 19 and 20 (stippled bar) were identified by voltage-clamp recording of injected oocytes.

B. RNA from these fractions was used to construct a cDNA library in the bacteriophage expression vector λ ZAP in which cDNA inserts (hatched rectangle) are flanked by promoters for T3 and T7 RNA polymerases (black boxes). DNA derived from pools of clones was digested with the restriction endonuclease Not I, cleaving the DNA at the position shown.

C. These truncated DNA templates were transcribed in vitro with T7 RNA polymerase in the presence of the cap precursor GpppG to produce functional RNA copies of the cDNA inserts.

D. Xenopus oocytes were injected with this RNA, cultured for three days, and assayed for sensitivity to serotonin by voltage-clamp recording of 5HT-activated currents.

E. A pool of cDNA clones giving a positive response was identified and progressively subdivided into smaller pools (sib selection) until a single positive clone was obtained.

Figure 4A:
Figure 4B:
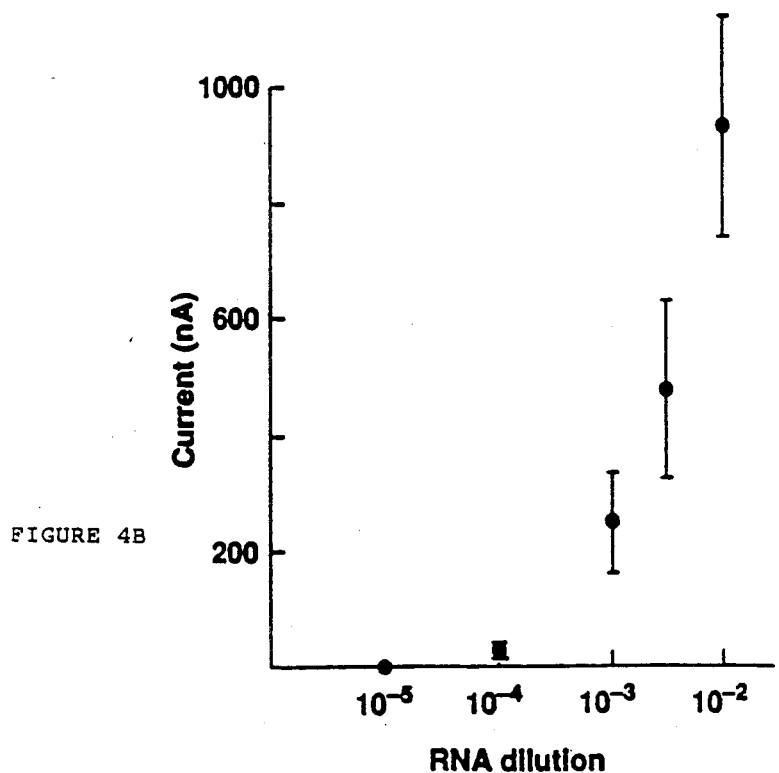

FIG. 4. Expression of functional serotonin receptors in Xenopus oocytes after injection of choroid plexus poly A+ RNA.

A. Voltage clamp recording from a Xenopus oocyte injected with 0.5 ng poly A+ RNA ($10^{-2}$ dilution) isolated from rat choroid plexus. The oocyte membrane potential was maintained at $-50$ mV, and serotonin ($10^{-6}$ M) was applied by superfusion for the duration indicated.

B. Current responses evoked by application of serotonin ($10^{-6}$ M) in oocytes injected with progressive dilutions of rat choroid plexus poly A+ RNA. The RNA stock was at an initial concentration of 1 ng/nl. Each oocyte was injected with 50 nl of diluted RNA, incubated for 3 days, and voltage-clamped at $-50$ mV. Detectable serotonin-induced membrane currents were obtained reliably with dilutions of up to 1 in $10^4$ poly A+ RNA. Plots indicate mean and standard error of serotonin-evoked currents obtained from 2–6 oocytes.

Figure 5:
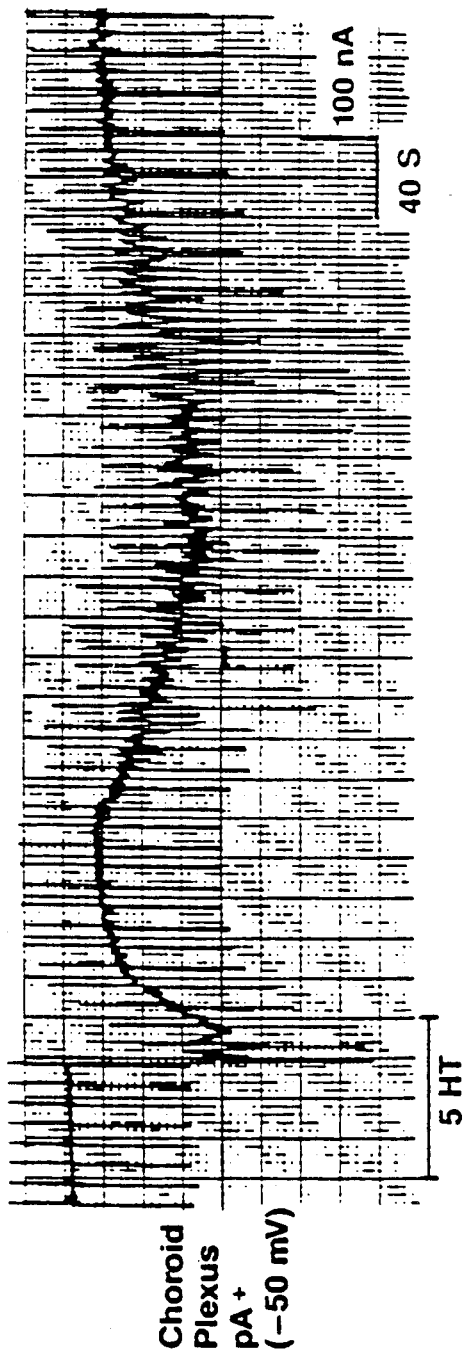

FIG. 5. Characteristic responses to serotonin by Xenopus oocytes injected with natural or synthetic RNA. Typical response to $10^{-6}$ M serotonin of a choroid plexus mRNA-injected oocyte.

Figure 6:
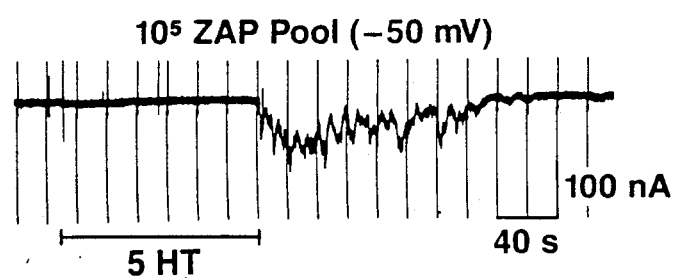

FIG. 6. Response to $10^{-6}$ M serotonin of an oocyte injected with RNA prepared in vitro from a pool of 100,000 cDNA clones.

Figure 7:
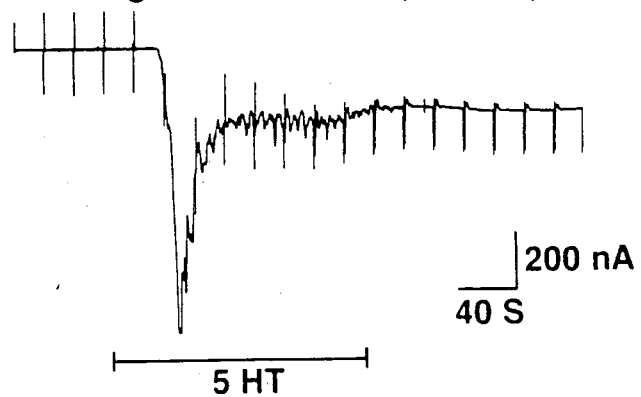

FIG. 7. Response to $10^{-6}$ M serotonin of an oocyte injected with RNA prepared in vitro from a single cDNA clone (Z347).

Figure 8:
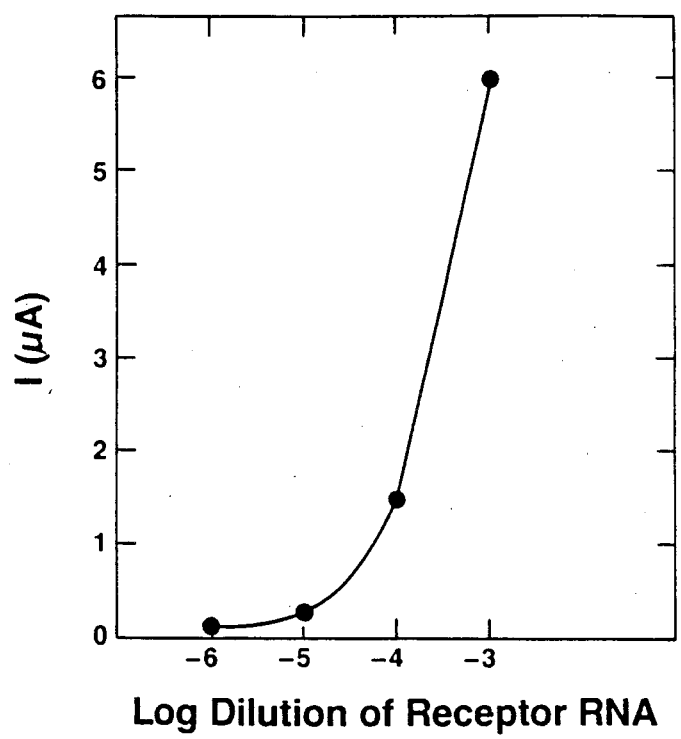

FIG. 8. Injection of RNA from pSR-1c cDNA clone confers serotonin sensitivity in Xenopus oocytes. Transcription of RNA was performed as described in Experimental Details, and dilutions of an RNA stock (1 mg/ml) were injected into Xenopus oocytes. Voltage clamp analysis was performed 24–48 hours after injection and the mean serotonin-induced current plotted as a function of progressive dilution of receptor RNA. Serotonin-induced membrane current could be detected reliably at dilutions of 1 in $10^5$ of transcribed RNA (10 ng). For further details see Experimental Details.

Figure 9A:
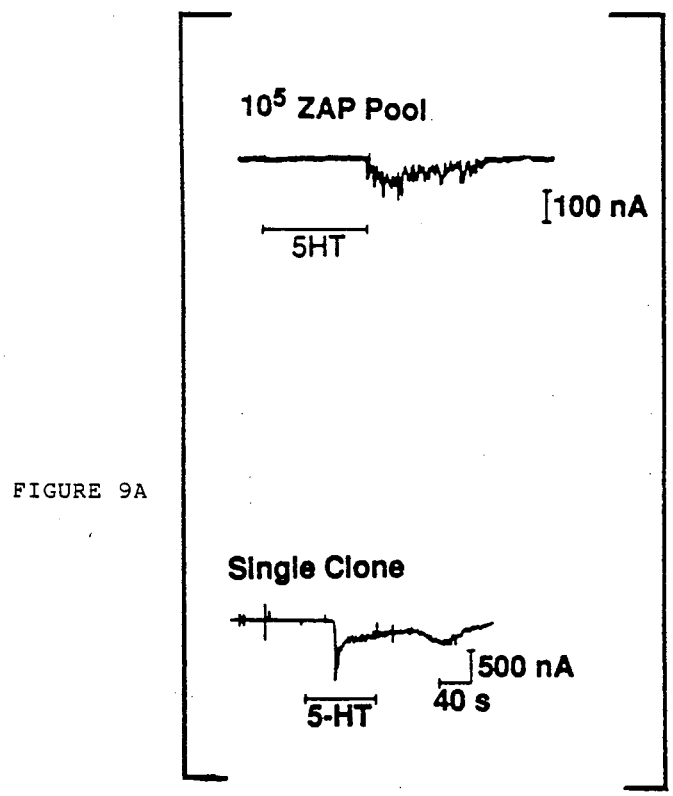

FIG. 9. Serotonin sensitivity of Xenopus oocytes injected with RNA transcribed in vitro from λ ZAP cDNA clones.

A. Inward current evoked by serotonin ($10^{-6}$ M) in oocytes injected with RNA transcribed from a pool of $10^5$ λ ZAP cDNA clones (approximately 100 ng) (top trace) and from a single λ ZAP cDNA clone (pSR-1c) at $10^{-4}$ dilution (5 pg) (bottom trace). Both oocytes were held at $-50$ mV.

B. Serotonin-evoked currents after serial dilution of RNA transcribed in vitro from the λ ZAP cDNA clone pSR-1c. The undiluted RNA was at a concentration of 1 ng/nl. Each oocyte was injected with 50 nl of diluted RNA. Cells were incubated for 3 days and voltage-clamped at $-50$ mV. Each point represents the mean and standard error of serotonin-evoked currents obtained from 3–7 oocytes.

Figure 10:
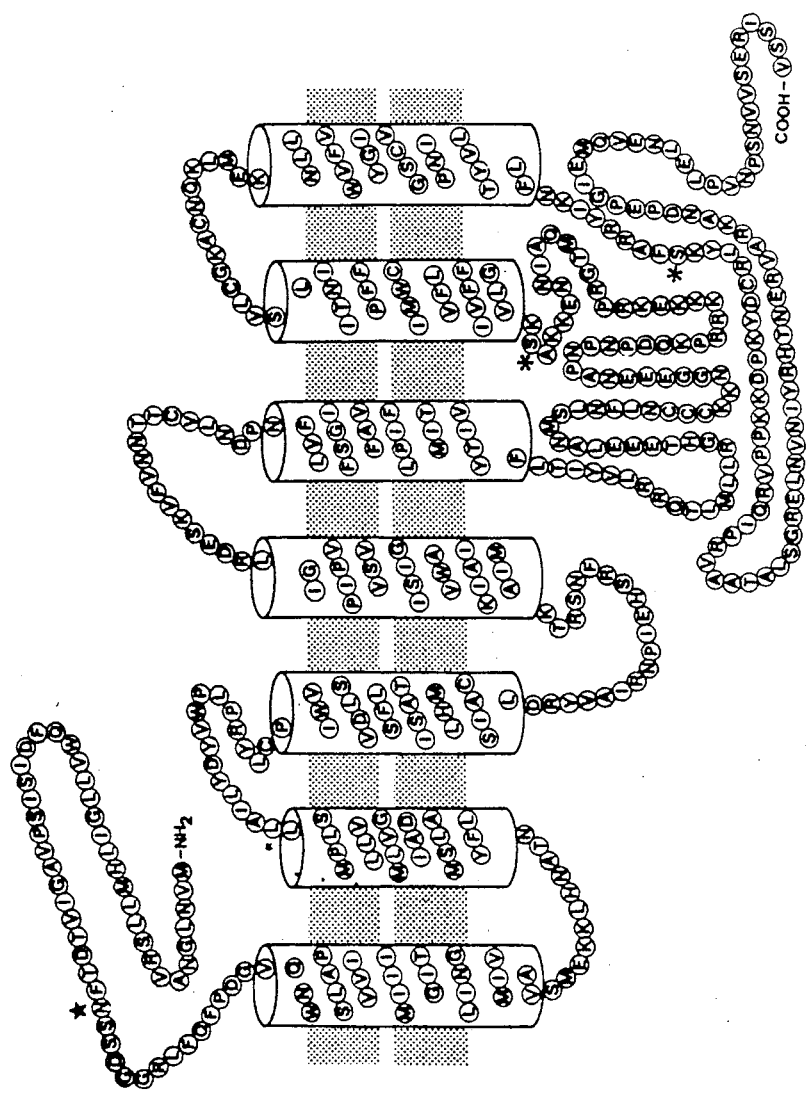

FIG. 10. A model for the transmembrane topology of the rat 5HT1c receptor. The receptor is shown as containing seven hydrophobic transmembrane regions. By analogy with the structure of rhodopsin, the amino terminus is located on the extracellular face of the lipid bilayer and the carboxyl terminus is located on the cytoplasmic side. Asterisks indicate serine residues that represent potential phosphorylation sites. The star indicates an asparagine residue in the amino terminal region that is a potential N-glycosylation site.

Figure 11:
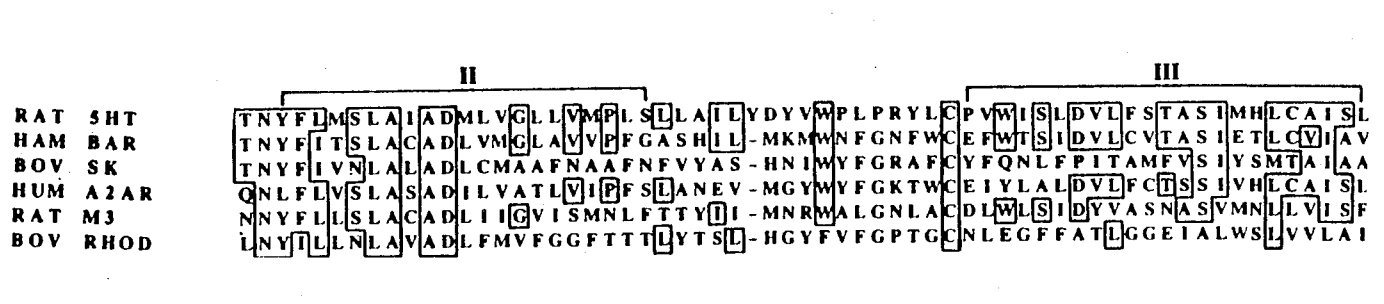

FIG. 11. Alignment of the amino acid sequence of the rat 5HT1c receptor (top), hamster $\beta_2$-adrenergic receptor (BAR, second row) (64), bovine substance K receptor (SK, third row) (30); human $\alpha_2$ adrenergic receptor (A2AR, fourth row) (65); rat muscarinic M3 receptor (M3, fifth row) (66); and bovine rhodopsin (RHOD, sixth row) (42). The amino acid residues enclosed by solid lines represent residues that are identical in at least 2 of the 5 reference sequences when compared to the 5HT1c receptor. Sequences present in the highly variable third cytoplasmic loop are not included, but the number of residues present in this loop is indicated in parentheses. The first 25 amino acids of the rat M3 sequence have not been included here. Roman numerals and brackets denote the seven putative transmembrane domains.

Figure 12:
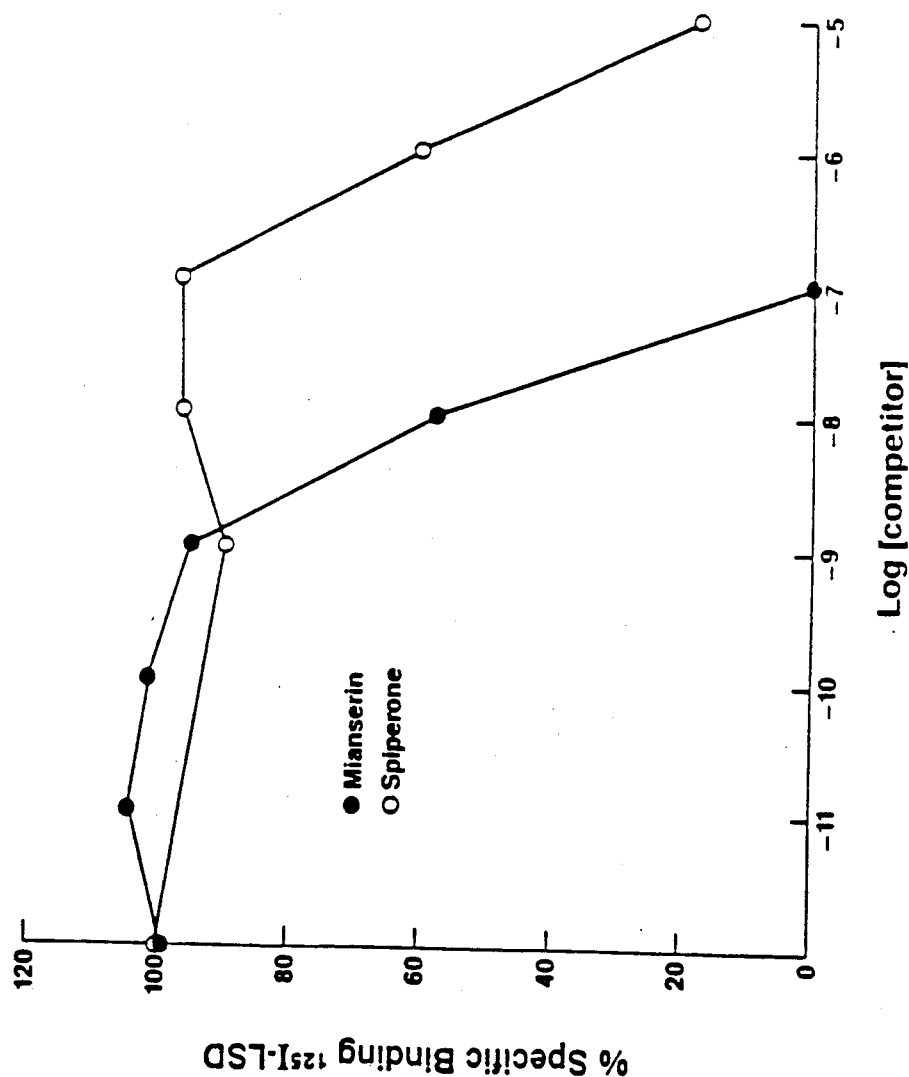

FIG. 12. Expression of $^{125}$I-LSD binding sites on SR3T3 cells and the pharmacological profile of ligand specificity. Membranes were prepared from control NIH3T3 cells and from SR3T3 cells expressing pSR-1c cDNA inserted into the retroviral expression vector pMV7 (2). $^{125}$I-LSD (1 nM) was incubated with 0.2 mg membrane protein aliquots suspended in Tris-HCl buffer. No specific binding was observed with untransfected control NIH3T3 cells, determined by addition of $10^{-5}$ unlabeled serotonin. In contrast, SR3T3 membranes exhibited 60–70% specific $^{125}$I-LSD binding, when determined by addition of unlabeled serotonin ($10^{-5}$M) or by comparison with untransfected 3T3 cells. The IC$_{50}$s for inhibition of $^{125}$I-LSD binding by mianserin and spiperone were also determined by addition of unlabeled drugs for 5 minutes prior to and during addition of $^{125}$I-LSD. Each point represents the mean determinations. Similar results were obtained in two separate experiments.

Figure 13A:
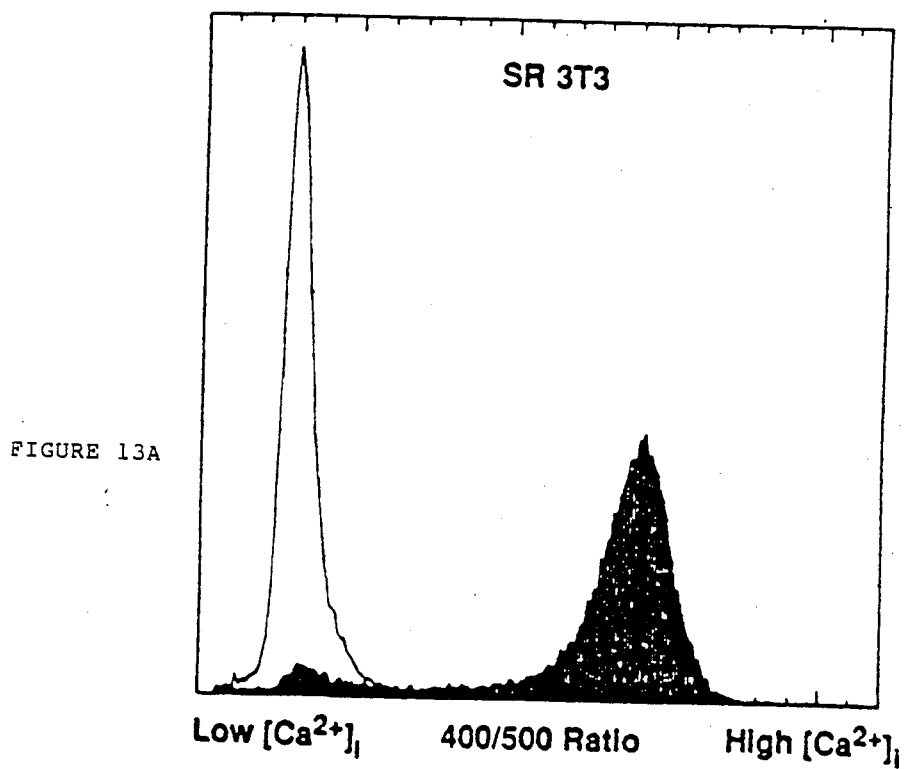
Figure 13B:
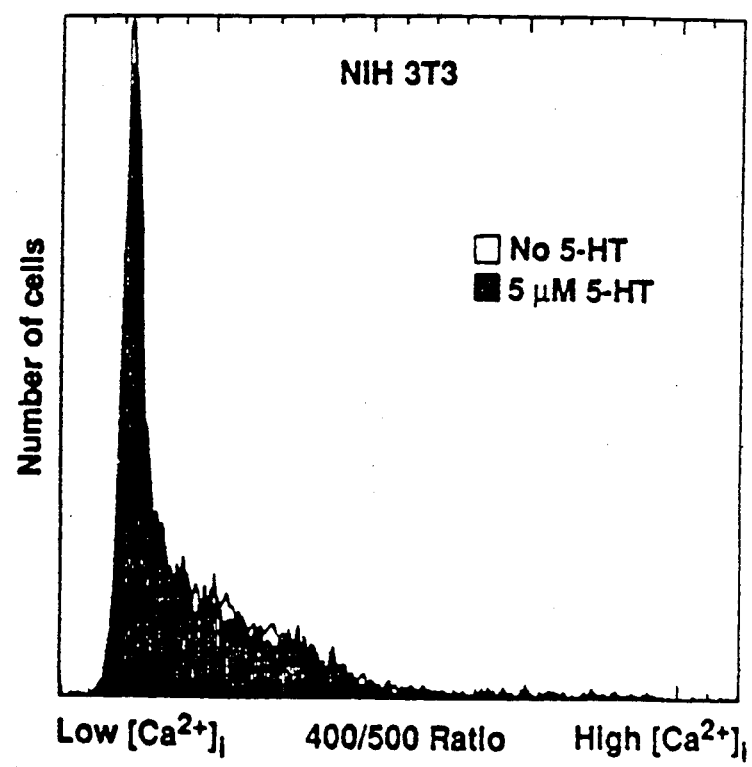

FIG. 13. Activation of 5HT1c receptors in transformed fibroblasts elevates intracellular $Ca^{2+}$ concentration. Untransformed cells (NIH3T3) or transformed cells expressing pSR-1c cDNA (SR3T3) were loaded with the $Ca^{2+}$-sensitive dye indo-1. Changes in the level of intracellular free-$Ca^{2+}$ following exposure to 5 μm serotonin (hatched peak) were monitored with a flow cytometer to measure the ratio of emissions at 400 and 500 nm. In each case, the resting intracellular $Ca^{2+}$ concentration in the absence of serotonin is also shown (open peak). For NIH3T3 cells, the two peaks are coincident. For SR3T3 cells, 95% of the population showed an elevation in intracellular $Ca^{2+}$ in the presence of serotonin. The mean resting $Ca^{2+}$ concentration in NIH3T3 and SR3T3 cells was similar.

Figure 14:
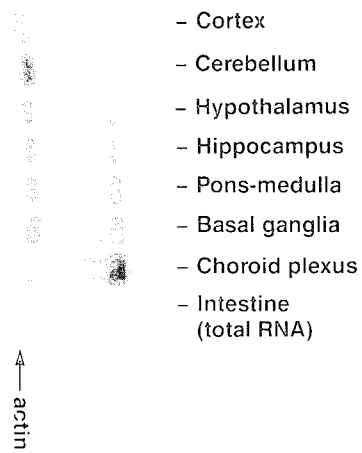
Figure 15:
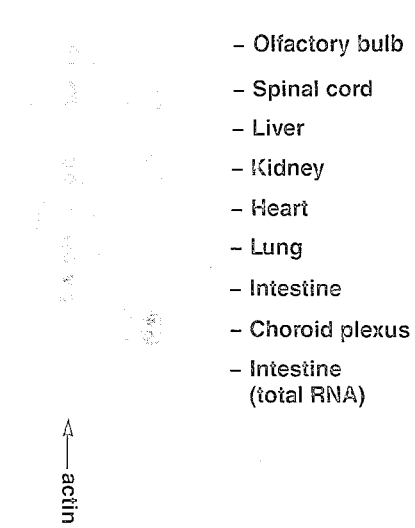

FIGS. 14 and 15. RNA blot analysis of the tissue distribution of 5HT1c receptor mRNA. Poly A+ RNA (2–20 μg) prepared from different brain regions (FIG. 14) and peripheral tissues (FIG. 15) (7, 34) was subjected to electrophoresis through an 0.8% agarose-formaldehyde gel, blotted onto Gene Screen (New England Nuclear) and hybridized with a $^{32}$P-labeled probe prepared from the 3 kb EcoRI cDNA insert from pSR-1c. Tissue regions are indicated above each lane. Filters were again hybridized with a $^{32}$P-labeled human α-actin probe to assess relative amounts of RNA loaded in each lane. The 5HT1c mRNA was judged to be approximately 5.2 kb, using 18S and 28S ribosomal RNA as standards.

DETAILED DESCRIPTION OF THE INVENTION

This invention relates to the cloning and isolation of DNA encoding a functional 5HT1c receptor. Although the specific DNA molecule which has been cloned is of rat origin, those skilled in the art will readily appreciate that such cloned rat DNA may be used as a hybridization probe to recover DNA encoding the serotonin 5HT1c receptor from other sources including specifically other mammalian sources, and most particularly human sources.

Figure 1:
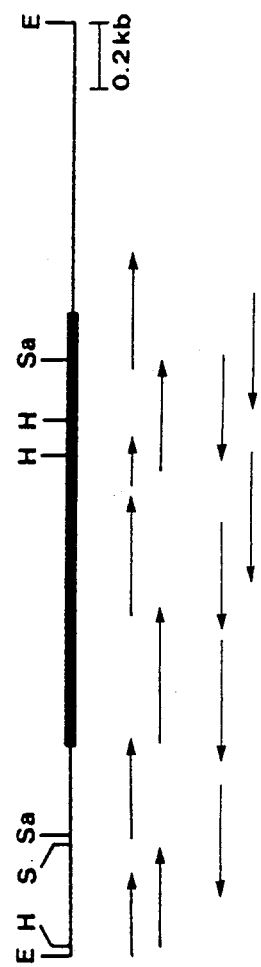
FIG. 1. Nucleotide sequence and deduced amino acid sequence of the rat 5HT1c receptor. The sequencing protocol is shown diagramatically. Sequences were determined for individual restriction fragments after subcloning into M13 vectors or with synthetic oligonucleotides as internal primers. The coding region is indicated by the heavy bar. Restriction sites are shown as indicated (E=EcoRI, H=Hind III, S=Sal I, Sa=Sac I). Numbers in the left-hand margin indicate nucleotide position. DNA sequence of cDNA clone pSR-1c was determined by the chain termination method of Sanger et al. (1).
Figure 3A:
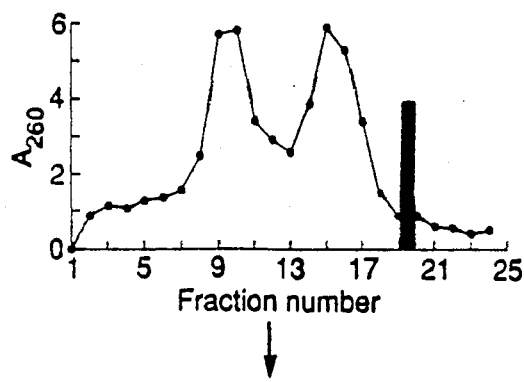
FIG. 3. Cloning strategy for isolation of a functional 5HT1c cDNA clone.
Figure 3B:
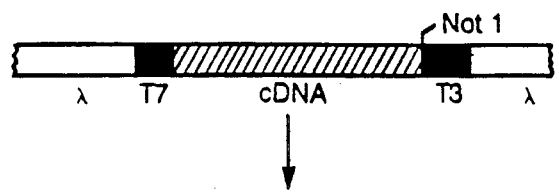
Figure 3C:
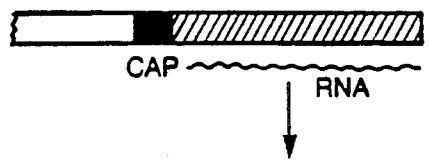
Figure 3D:
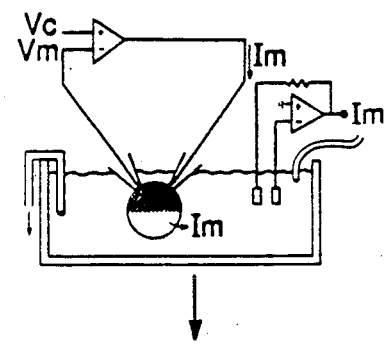
Figure 3E:

In one embodiment this invention provides cDNA encoding a functional serotonin 5HT1c receptor, e.g., the cDNA having the nucleic acid sequence shown in FIG. 1.

In another embodiment this invention provides for the first time a means for obtaining isolated, functional serotonin 5HT1c receptor by expressing DNA, such as cDNA encoding the receptor in a suitable host, such as a bacterial, yeast, or mammalian host cell using methods well known in the art and recovering the functional serotonin 5HT1c receptor after it has been expressed in such a host, again using methods well known in the art.

In a further embodiment this invention provides cloned DNA encoding serotonin 5HT1c receptor, typically cloned into a plasmid such as pBR322 or into a bacteriophage, such as λ bacteriophage. One example of such a plasmid is the plasmid pSR-1c described in greater detail hereinafter and deposited with the American Type Culture Collection (ATCC) in *Escherichia coli* under the designation DJ200 and under ATCC Accession No. 67636. This deposit and the other deposit made in connection with this invention were made pursuant to, and in satisfaction of the provisions of the Budapest Treaty On The International Recognition of The Deposit of Microorganisms For The Purposes of Patent Procedure and were made with the American Type Culture Collection (ATCC), 12301 Parklawn Drive, Rockville, Maryland 20852.

In a still further embodiment, this invention provides plasmids adapted for expression in a mammalian cell which comprises DNA, e.g., cDNA, encoding functional serotonin 5HT1c receptor and the regulatory elements necessary to express such DNA in the mammalian cell. Once again, those skilled in the art will readily appreciate that numerous plasmids may be constructed utilizing existing plasmids and adapted as appropriate to contain the regulatory elements necessary to express the DNA in the mammalian cell. In this regard numerous mammalian cells may be used including, for example, the mouse fibroblast cell NIH 3T3, CHO cells, HeLa cells, etc. One example of such a plasmid is the plasmid designated pMV7-347 described more fully hereinafter which was constructed from the plasmid pSR-1c already mentioned and the plasmid pMV7 described in detail by Maddon, et al. (2).

Such expression plasmids may be used to transfect mammalian cells or DNA encoding the serotonin 5HT1c receptor may be otherwise introduced into mammalian cells, e.g., by microinjection, to obtain mammalian cells which comprise DNA, e.g., cDNA or a plasmid, encoding the serotonin 5HT1c receptor. In one presently preferred embodiment this invention provides an NIH3T3 cell transfected with the plasmid pMV7-347 which has been designated SR3T3 and deposited under ATCC Accession No. CRL 9651.

This invention further provides a method for determining whether a ligand, such as a known or putative drug, is capable in vivo of binding to functional serotonin 5HT1c receptor. This method comprises (a) contacting a mammalian cell, such as the SR3T3 cell, expressing functional serotonin 5HT1c receptor on its surface, with the ligand under conditions which are known to prevail, and thus to be associated with, in vivo binding of the ligands to the serotonin 5HT1c receptor, (b) detecting the presence of any of the ligand being tested bound to the serotonin 5HT1c receptor on the surface of the cell, and (c) thereby determining whether the ligand binds to the serotonin 5HT1c receptor.

This invention still further provides a method of detecting the expression of the serotonin 5HT1c receptor by a cell, particularly on the surface of the cell, such as a human brain cell, which comprises obtaining total mRNA from the cell using well known methods and contacting the mRNA so obtained with the DNA, e.g., cDNA, encoding the serotonin 5HT1c receptor under hybridizing conditions, detecting the presence of mRNA hybridized to the cDNA, and thereby detecting the expression of the serotonin 5HT1c receptor by the cell.

This invention also provides a DNA probe useful for detecting in a sample, such as a sample of human brain cells, nucleic acid encoding the serotonin 5HT1c receptor. Such a probe comprises a nucleic acid molecule of at least about 15 nucleotides having a sequence complementary to a sequence included within the sequence shown in FIG. 1. Such nucleic acid probe technology is well known to those skilled in the art who will readily appreciate that such probes may vary greatly in length and may be labeled with a detectable label, such as a radioisotope or fluorescent dye, to facilitate detection of the probe.

In yet another embodiment this invention provides an antibody directed to the serotonin 5HT1c receptor. Such an antibody may be serum-derived or monoclonal and may be prepared using methods well known in the art. For example, cells such as SR3T3 cells may be used as immunogens to raise such an antibody. Alternatively, synthetic peptides may be prepared using commercially available machines and the amino acid sequence shown in FIG. 1. As a still further alternative, DNA, such as a cDNA whose sequence is shown in FIG. 1 or a fragment thereof, may be cloned and expressed and the resulting polypeptide recovered and used as an immunogen. In one embodiment the antibody is a monoclonal antibody directed to an epitope of the serotonin 5HT1c receptor present on the surface of a cell and having an amino acid sequence included within the amino acid sequence shown in FIG. 1.

Still further this invention provides a method of detecting the presence of the serotonin 5HT1c receptor on the surface of a cell which comprises contacting the cell with a monoclonal or serum-based antibody directed to an exposed epitope on the receptor under conditions permitting binding of the antibody to the receptor, and detecting the presence of the antibody bound to the cell, and thereby the presence of the serotonin 5HT1c receptor on the surface of the cell. Such a method is useful in determining whether a given cell, particularly a given brain cell, is defective relative to the expression of functional 5HT1c receptor on the surface of the cell.

Finally this invention provides a method of screening drugs to identify drugs which specifically interact with, and bind to, the serotonin 5HT1c receptor on the surface of a cell. This method comprises contacting a mammalian cell which is expressing functional serotonin 5HT1c receptor with a plurality of drugs, known or putative, determining those drugs which bind to the mammalian cell, and thereby identifying drugs which specifically interact with, and bind to, the serotonin 5HT1c receptor.

As a first step in determining the structure and function of serotonin receptors, a cDNA clone encoding one of these subtypes, 1c, has been isolated. This particular species was chosen for two reasons: (i) it is highly expressed in a particular brain subregion; and (ii) it couples to an intracellular signaling pathway compatible with its ability to be functionally expressed in *Xenopus laevis* oocytes.

Autoradiographic analysis of brain sections using a variety of radioligands ($^3$H-mesulergine, $^3$H-serotonin and $^{125}$I-LSD) led to the discovery of the 5HT1c receptor and identified the choroid plexus as a site of high receptor density. This vascularized, non-neuronal tissue sits in the ventricles of the brain, where it produces much of the cerebrospinal fluid. High resolution autoradiography has localized 5HT1c receptors to the epithelial cell layer of the choroid. Quantitative binding studies have shown that the specific activity of $^{125}$I-LSD binding sites is at least 10-fold higher in the rat choroid plexus than in any other tissue examined. It has also been shown that serotonin can stimulate the hydrolysis of phosphatidylinositol in the choroid plexus and that this effect is mediated through its interaction with the 5HT1c receptor.

Lacking any biochemical or immunological tools with which to purify or easily detect serotonin receptors, a functional assay has been employed as the basis for identifying a cDNA clone encoding this receptor. Miledi and co-workers were the first to show the utility of *Xenopus laevis* oocytes as an expression system for studying neurotransmitter receptors and ion channels from mammalian brain (4, 5). The microinjection of brain poly A+ RNA into these cells leads to the appearance of functional receptors at the cell surface, and renders the oocyte responsive to a number of neurotransmitters, including serotonin. Using two electrode voltage clamp techniques, this response can be detected electrophysiologically as an inward membrane current carried by chloride ions. Detailed analysis of the mechanism involved has shown that the application of serotonin leads to the hydrolysis of phosphatidylinositol-4,5-biphosphate and the production of inositol triphosphate ($IP_3$). $IP_3$ then evokes the release of calcium from intracellular stores, leading to the opening of endogenous calcium-dependent chloride channels located in the oocyte plasma membrane. More recently, Lubbert, et al. have shown that following injection of rat brain mRNA into oocytes the predominant serotonin receptor subtype detected is 5HT1c. They have also demonstrated that the rat choroid plexus is enriched for 5HT1c receptor message, and that electrophoretic fractionation of plexus RNA yields a partially purified preparation in the 5 to 6 kb size range which encodes an active receptor. Using a hybrid-depletion procedure, in combination with the oocyte assay, this group has isolated a partial 5HT1c receptor cDNA clone from a mouse choroid plexus library (6).

Specifically, this invention relates to the first isolation of a functional cDNA clone encoding a 5HT1c receptor, e.g., the rat 5HT1c receptor, using the oocyte expression assay to screen in vitro transcripts generated from a choroid plexus cDNA expression library. The serotonin receptor is shown to belong to the family of rhodopsin-like signal transducers which are distinguished by their seven-transmembrane configuration and their functional linkage to G-proteins. A mammalian cell line expressing functional 5HT1c receptors at the cell surface has been constructed, as determined by pharmacologic and physiologic methods, thus establishing the first well-defined, cultured cell line with which to study a particular serotonin receptor sub-type. It has been found that the 5HT1c receptor is present throughout the central nervous system, implying that it may be involved in a variety of neuronal functions.

The invention will be better understood by reference to the Experimental Details which follow, but it will be readily appreciated by those skilled in the art that these examples are only illustrative of the invention as described more fully in the claims which follow thereafter.

EXPERIMENTAL DETAILS

The cloning of most neurotransmitter receptors has required the purification of receptor, the determination of partial protein sequence and the synthesis of oligonucleotide probes with which to obtain cDNA or genomic clones. However, the serotonin receptors have not been purified and antibodies to the receptors have not been generated. Applicants have therefore designed a cDNA expression system that permits identification of functional cDNA clones encoding serotonin receptors in the absence of protein sequence information. A similar approach has been used to isolate a cDNA encoding the bovine neuropeptide substance K receptor (30).

Applicants' cloning strategy (FIG. 3) is based on quantitative considerations of the following findings. High levels of serotonin 5HT1c receptors ($10^5$ per cell) are expressed in the choroid plexus (3, 31), a nonneuronal cell type in the central nervous system associated with the production of cerebrospinal fluid. Xenopus oocytes injected with choroid plexus mRNA exhibit a serotonin-evoked inward current. Application of serotonin appears to liberate inositol phosphates that raise intracellular $Ca^{2+}$ levels, leading to the opening of $Ca^{2+}$-dependent chloride channels (5, 6, 28). Patch clamp recording has demonstrated that the conductance of a single serotonin-activated chloride channel is about 3 pS (28). Thus, the opening of $10^6$ chloride channels will result in the generation of a readily detectable current of 100 nA. Assuming that the translational efficiency of the oocyte approximates that of a plexus cell, injection of RNA from ten plexus cells, or as little as 2 pg of poly A+ RNA, should lead to the expression of $10^6$ serotonin receptors on the oocyte surface. Parenthetically, the amplification of signaling usually associated with G protein coupled receptors (32, 33) suggests that considerably fewer than $10^6$ receptors need be occupied to open $10^6$ chloride channels. To determine experimentally the sensitivity of the oocyte expression assay, oocytes were injected with serial dilutions of poly A+ RNA isolated (7, 34) from the rat choroid plexus. Injection of as little as 5 pg of poly A+ RNA (or 5 fg of pure receptor mRNA, assuming 0.1% abundance) was sufficient to generate an inward current of about 100 nA (FIG. 4). Since it is possible to inject up to 50 ng of RNA into an oocyte, it should be possible to detect a cDNA clone encoding the 5HT1c receptor, even if present at an exceedingly low frequency in a cDNA expression library.

A cDNA library was therefore constructed from choroid plexus mRNA in λ ZAP, a vector permitting the in vitro transcription of cDNA inserts. RNA transcribed from populations of cDNA clones were screened for their ability to induce serotonin-evoked currents in Xenopus oocytes. A single clone encoding a functional serotonin 5HT1c receptor was purified from a large population of clones by procedures of sib selection (FIG. 3).

Materials

Female, oocyte-positive *Xenopus laevis* frogs were obtained from Xenopus I and collagenase from Worthington.

λ ZAP and T3 RNA polymerase were purchased from Stratagene. T7 RNA polymerase and diguanosine triphosphate (GpppG) was purchased from Pharmacia, and AMV reverse transcriptase was purchased from Life Sciences, Inc. All other reagents used for cDNA synthesis or in vitro transcription were supplied by Pharmacia, New England Biolabs or Boeringer-Mannheim. Ultra-pure sucrose (RNAse free, for density gradients) was obtained from Schwarz/Mann, Inc.

Serotonin was purchased from Sigma, $^{125}$-I-LSD from Dupont/NEN.

Microinjection of Xenopus oocytes

Oocytes were surgically removed from frogs and separated manually into small groups of 10 or 20. Cells were enzymatically dissociated by treatment in Barths medium containing 2% Ficoll (w/v) and 2 mg/ml collagenase, for 2 hours at room temperature with constant agitation. Oocytes were stored in Barths containing 2% Ficoll, penicillin and streptomycin, at 18° C. Cells were typically injected with between 50 and 100 nl of sample. Microinjection pipettes were pulled from 25 μl capillaries (Drummond) using a vertical microelectrode puller. A Narishige manipulator, fitted with a simple ClayAdams micropipette was used as the injection device.

Oocytes were injected while under Barths with Ficoll and incubated at 18° C. for 1-3 days before assaying.

Electrophysiology

Oocytes injected 1 to 3 days prior to recording were placed in a continuous-flow chamber perfused with frog Ringer solution. All drugs were introduced through this system by switching the perfusion line inlet. The membrane potential of the oocyte was voltage-clamped at $-50$ mV with two microelectrodes (2-5 megohm resistance; filled with 3M KCl) using an Axoclap 2A with virtual ground and a remote switchable headstage. Membrane currents were recorded through the virtual ground and filtered at 10 Hz. Responses were either digitized at 5 Hz and stored on a PDP 11/73 microcomputer or recorded on a Gould chart recorder.

RNA isolation and Northern blot analysis

RNA was extracted from tissues by homogenization in guanidinium and precipitation with LiCl, as described by Cathala et al. (7). Polyadenylated RNA was prepared by one cycle of binding to oligo(dT)-cellulose (Pharmacia, Type 7).

Northern analysis of RNA samples was carried out according to Krumlauf et al. (8).

Sucrose gradient fractionation of choroid plexus RNA

Approximately 250 μg of total RNA, extracted from choroid plexus tissue obtained from 12 adult rats, was dissolved in 200 μl of 0.1% SDS, 5 mM Tris-HCl (pH 7.3), 0.5 mM EDTA and loaded onto a 12-ml linear sucrose gradient (35) [5-25% (w/v) sucrose containing 0.1M NaCl, 10mM Tris-HCl (pH 7.3), 0.5% SDS, 1 mM EDTA]. The sample was centrifuged in a Beckman SW 41Ti ultracentriplefuge rotor at 21,000 rpm for 15.5 hours at 22° C. 0.45 ml fractions were collected manually from the top and the RNA recovered by ethanol precipitation. Each sample was dissolved in 20 μl of water, 1 μl was removed for oocyte injection and the remainder was stored at 80° C.

cDNA library construction

Positive fractions from the sucrose gradient were combined and the RNA concentrated by ethanol precipitation. The first strand of cDNA was synthesized using oligo-(dT)$_{12-18}$ formation (Pharmacia) as a primer (36) and actinomycin D to reduce hairpin formation. The second strand was synthesized according to the method of Okayama and Berg (9). The double-stranded cDNA was methylated with EcoRI methylase and the ends flushed with T4 DNA polymerase. Phosphorylated EcoRI linkers (Pharmacia) were ligated to the cDNA and excess linkers were cleaved off with EcoRI (37). cDNA was separated from free linkers by chromatography on Ultragel AcA 34 (LKB) (38). cDNAs were inserted into the EcoRI site of λ ZAP (Stratagene) according to the instructions of the manufacturer. Recombinant bacteriophage was propagated using the bacterial strain supplied by Stratagene (BB4) and Bluescript plasmids were rescued from ZAP clones by M13 excision according to the instructions of the manufacturer.

Preparation of λ DNA for in vitro transcription

The cDNA library was amplified in pools of 20,000 clones. Recombinant phage were eluted from each plate (150 mm) in 15 ml SM and kept separate. The majority of each phage stock (14 ml) was used to prepare DNA by a standard protocol (40). Each DNA sample was treated DNase-free RNase A (50 μg/ml, 37° C., 30 min), followed by digestion with proteinase K (100 μg/ml, 37° C., 30 min). After a series of phenol and chloroform-isoamyl alcohol extractions, the DNA was concentrated by ethanol precipitation. When, in the course of sib selection, the pool size was reduced to 2000 clones, or smaller, phage stocks had to be re-amplified in order to obtain sufficient amounts of DNA for transcription. For the initial screen, DNA derived from five pools of 20,000 clones was combined so as to represent $10^5$ clones per sample.

Prior to transcription, approximately 20 μg of each DNA sample was digested to completion with the restriction endonuclease Not I, cleaving each recombinant molecule downstream from the T7 promoter and after the cDNA insert. This was followed by proteinase K digestion (100 μg/ml, 37° C., 30 min.), organic (phenol-chloroformisoamyl alcohol) extraction and ethanol precipitation. DNA was dissolved in 5 μl TE.

In vitro transcription

Transcriptions were carried out in a 50 or 100 μl reaction volume at 40° C. and contained 20 μg DNA template, 40 mM Tris-HCl (pH 7.9), 7 mM $MgCl_2$, 10 mM DTT, 2 mM spermidine, 10 mM NaCl, 25 μg/ml BSA, 2000 units/ml human placental RNase inhibitor, 0.5 mM ATP, CTP and UTP, 0.2 mM GTP, 1 mM GpppG and 70 units T7 RNA polymerase. Incubation was for 1-2 hours. The reaction was terminated by extraction with phenol-chloroform mixture, followed with a chloroform extraction. Nucleic acid was recovered by ethanol precipitation and the pellet was dissolved in a small volume of water, usually 5 μl for microinjection into oocytes. A small amount of alpha-$^{32}$P-UTP was included in the reaction cocktail to monitor the extent of RNA synthesis, which was determined by TCA-precipitation of a small aliquot of the reaction products. Typically, between 3 and 10 μg of RNA was synthesized in these reactions, making the RNA/cDNA ratio roughly 5.

DNA sequencing

The DNA sequence of pSR-1c cDNA was determined by the chain termination method of Sanger et al. (1).

Gene transfer

Transfection of NIH3T3 cells with pMV7-347 DNA was done by the standard method of calcium phosphate precipitation (10). Transformants were selected in DME supplemented with 10% calf serum (HyClone) and 1 mg/ml neomycin (G418; Difco).

Flow cytometry analysis of serotonin-induced changes in intracellular $Ca^{2+}$ concentration Cells were removed from plates by treatment with $Mg^{2+}$- and $Ca^{2+}$-free Hepes buffered Hanks saline containing 0.5 mM EDTA.

Cells were loaded with Indo-1 in normal Hanks buffer supplemented with 0.1% BSA, 0.1% glucose and 10 μm Indo-1 ester at 37° C. for 5 minutes. Cells were washed in Hanks and resuspended at $2.5 \times 10^5$ per ml, and analyzed using an Epics 753 flow cytometer. The intracellular Indo-1 was excited with an Innova 90-5 argon ion laser emitting 100 mW at 363 nm wavelength. The fluorescence emission was split with a 448 dichroic filter and detected with photomultipliers with 400.5 nm bandpass and 500 nm bandpass filters. Cells and serotonin (10 μM) were held in separate syringes and mixed in a "Y" connector just prior to entering the flow chamber. Further details of this method are given in Schieren and MacDermott (11).

$^{125}$-I-LSD binding assays

Preparation of crude membranes and binding assays were carried out essentially as described by Yagaloff, et al. (3). $^{125}$I-LSD (2200 Ci/mmol; 1 nM final concentration) was added to approximately 0.2 mg of membrane protein aliquot in 1 ml 50 mM Tris-HCl (pH 7.6), 10 μM pargyline, 5 mM EDTA, 1 mM ascorbate. 0.2 mg of crude membrane protein derives from approximately $2 \times 10^6$ cells. Non-specific binding of $^{125}$I-LSD (not displaceable by $10^{-7}$M mianserin) to membranes prepared from untransformed NIH3T3 cells represented approximately 45% of that obtained with SR3T3 membranes. Mianserin displaceable binding was in the order of 50,000 cpm $^{125}$I-LSD bound/mg protein. Samples were incubated, in the absence or presence of unlabeled competing drugs, at 37° C. for 15 minutes. Samples were collected by vacuum filtration onto Whatman GF/B filter discs, washed three times with 10 mls each of ice-cold Tris buffer and counted in an LKB gamma counter.

pSR-1c DNA was linearized with NotI or XhoI endonuclease and transcribed with T7 or T3 RNA polymerase to generate sense and anti-sense RNA probes, respectively. Transcription reactions (20 μl) contained 40 mM Tris-HCl (pH 7.5), 6 mM $MgCl_2$, 2 mM spermidine, 10 mM NaCl, 10 mM DTT, 30 units placental RNase inhibitor, 0.5 mM each of ATP, CTP, and GTP, 250 μCi $^{35}$S-UTP (1000 Ci/mmol; Amersham), and 2 μg linearized plasmid DNA and were incubated at 40° C., for 60 minutes. Template DNA was hydrolyzed with RQ1 DNase (Promega) according to the manufacturer. RNA probes were purified by two ammonium acetate-ethanol precipitations to give a final specific activity of $10^9$ cpm/μg.

The fixation of adult rat brains and preparation of tissue sections was done according to published procedures (61) with the following exceptions: Hybridization buffer consisted of 50% formamide, 0.6 M NaCl, 10 mM Tris-HCl (pH 7.5), 0.02% Ficoll, 0.02% polyvinyl pyrolidone, 0.1% BSA, 1 mM EDTA, 10 μg/ml salmon sperm DNA, 50 μg/ml yeast total RNA, 50 μg/ml yeast tRNA and $1 \times 10^7$ cpm/ml $^{35}$S-labeled probe. The final high-stringency wash contained 0.1 X SSC, 0.05% sodium pyrophosphate and 14 mM β-mercaptoethanol. Slides were dipped in Kodak NTB2 nuclear track emulsion (Eastman Kodak), exposed at 4° C., and developed in Kodak D-19 developer.

EXPERIMENTAL RESULTS

Isolation of a functional serotonin receptor cDNA clone

Oocytes were microinjected with serial dilutions of poly A+ RNA from the rat choroid plexus in order to estimate the sensitivity of the voltage clamp assay in measuring serotonin receptor activity (FIG. 4). The limit of detection is approximately 5 picograms, or the amount of mRNA equivalent to that which can be obtained from 20 mammalian cells. The ability to detect such low levels of receptor mRNA is a consequence of two factors, namely the signal amplification provided by the second messenger system, and the sensitivity of the voltage clamp method in measuring changes in membrane conductance.

Given the degree of sensitivity which can be achieved with the physiologic assay, it is possible to screen a choroid plexus cDNA library for a functional serotonin receptor clone by synthesizing capped RNAs in vitro and injecting these transcripts into oocytes. In view of the frequency predicted for obtaining a full-length 5-6 kb cDNA required for the expression of an active serotonin receptor, it is necessary to first enrich the message population to be used in the construction of the library. This was accomplished by the method of sucrose density sedimentation using total RNA isolated from the choroid plexus (9, 35, 36, 37, 38). Fractions collected from such a gradient were assayed for serotonin receptor mRNA by voltage clamp analysis of microinjected oocytes, revealing a positive peak in the high molecular weight range (see FIG. 3A). Consistent with reported data (6, 39), injection of RNA in the size range 5-7 kb resulted in a serotonin-evoked inward current in oocytes. The RNA thus obtained was used to construct a cDNA library in the cloning vector λZAP (9, 35, 36, 37, 38). This vector was chosen because bacteriophage T7 and T3 promoters flank the cDNA insertion site, enabling one to synthesize RNA transcripts in vitro from either direction. A size-enriched library representing 1.2 million clones was generated and DNA was prepared from pools of 20,000 recombinant phage. In order to expeditiously screen the library, DNA from five pools (i.e. 100,000 clones each) was combined, transcribed with T7 RNA polymerase (40) and the reaction products microinjected into oocytes. After a 3 day incubation period, the oocytes were subjected to voltage clamp analysis (this cloning scheme is summarized in FIG. 3). FIG. 5 shows the typical response to $10^{-6}$M serotonin of a choroid plexus mRNA-injected oocyte. FIG. 6 shows an initial positive response to $10^{-6}$M serotonin of an oocyte injected with RNA prepared in vitro from the pool of 100,000 cDNA clones; although relatively small (20-50 nA), this signal was believed to be genuine because there is no obvious source of false-positives or background noise. Further fractionation reduced the pool size step-wise by factors of ten, yielding a single cDNA clone (Z347) after four rounds of re-screening. At each stage, at least one pool of RNA generated serotonin-responsive currents. The magnitude of the serotonin-evoked current normalized per microgram of injected RNA increased as the sib selection proceeded. A response obtained from Z347 is shown in FIG. 7.

Figure 9B:
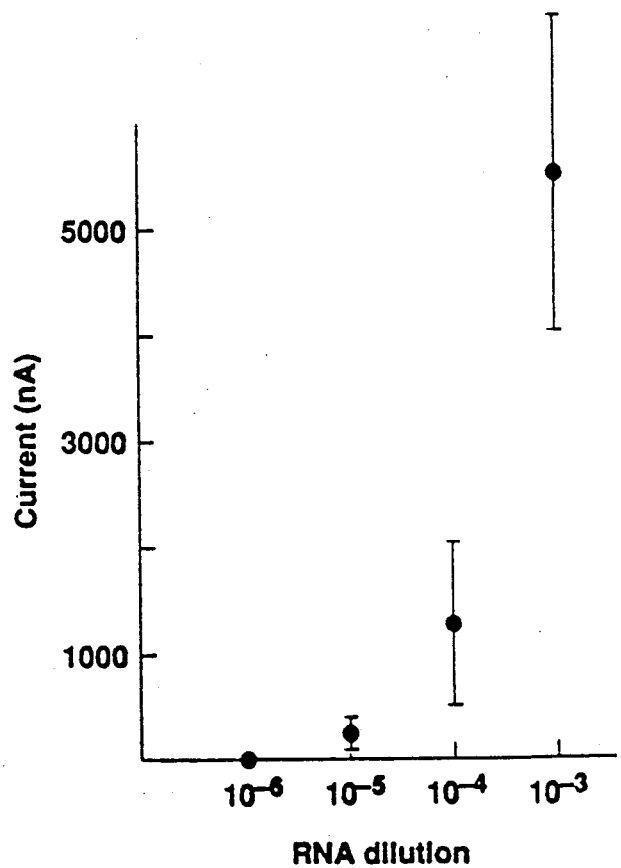

A plasmid containing the cDNA insert still flanked by T7 and T3 promoters (p347) was rescued from Z347 by a λ excision procedure. FIG. 8 shows the results of a dilution study in which various amounts of capped, synthetic RNA transcribed from pSR-1c DNA were injected into oocytes and the responses to serotonin recorded. The limit of detection falls at or near 0.5 pg of injected RNA, an amount sufficient to generate a serotonin-evoked current of about 200 nA (FIG. 9B). Assuming an average RNA size of 3 kb, this is roughly equivalent to $3 \times 10^5$ molecules per oocyte.

Pharmacologically, the rat choroid plexus 5HT1C receptor has been shown to bind the serotonin antagonists mianserin with high affinity ($K_i=15$ nM) and spiperone with substantially lower affinity ($K_i=6$ μM) (23). This rank order of drug potency has been established by three independent methods: (i) competitive binding studies with $^{125}$I-LSD to choroid plexus membranes; (ii) inhibition of serotonin-stimulated phosphatidyllinositol turnover in choroid plexus tissue; and (iii) inhibition of oocyte responses to serotonin following injection of rat choroid plexus mRNA. For oocytes injected with pSR-1c-derived RNA, 1 μM mianserin completely abolishes responses to 10 nM 5-HT, whereas 1 μM spiperone is barely effective as an antagonist (not shown). The relative potency of these antagonists is therefore similar when assayed against 5HT1c receptors present in the choroid plexus or in oocytes injected with pSR-1c-derived RNA. Applicants conclude that pSR-1c encodes the 1c subtype of serotonin receptor from the choroid plexus.

The nucleotide sequence and deduced amino acid sequence of serotonin receptor 1c The nucleotide sequence and deduced amino acid sequence of the 5HT1c receptor are shown in FIG. 1. In addition, FIG. 2 shows the percent of codon usage in the 5HT1c receptor DNA. One long open reading frame extending from an ATG codon at position 688 to a stop codon at residue 2068 can encode a protein sequence 460 amino acids in length, having a relative molecular size of 51,899 kD. Stop codons are found in all three frames upstream of this ATG, and downstream of the termination site. Interestingly, the coding sequence is preceded by a long 5' untranslated region with minimum length of 700 bp. The functional 5HT1c receptor cDNA cloned by applicants is only 3 kb whereas the mRNA containing this sequence is more than 5 kb. It is likely therefore that the cDNA clone does not extend to the 3' terminus of the mRNA, but terminates artificially in the 3'-untranslated region. In addition, nucleotides surrounding this putative initiation codon satisfy the consensus rules for a protein translation start site.

The 5HT1c receptor shares numerous sequence and structural properties with the family of receptor molecules that has been predicted to span the lipid bilayer seven times (FIG. 10). This family includes rhodopsin and related opsins (41), the α and β adrenergic receptors (42), the muscarinic cholinergic receptors (43), the substance K neuropeptide receptor (30), the yeast mating factor receptors (46, 47, 48), and the oncogene cmas (49). Each of these receptors is thought to transduce extracellular signals by interaction with guanine nucleotide-binding (G) proteins (42, 50, 51).

In addition to the similarity in transmembrane topology, the serotonin receptor shares blocks of homology with other receptors of its kind, particularly in areas which are known to be highly conserved among members of this family (see FIG. 1). For example, in the second transmembrane domain, there is a stretch of amino acids whose sequence is nearly invariant, and reads: —N—Y—F(I)—X—X—S(N)—L—A—X—A—D—L. In the case of the 5HT1c receptor sequence, this region is only slightly divergent from the consensus, reading: —N—Y—F—X—X—S—L—A—I—A—D—M—. Other invariant landmarks include: two cysteine residues, possibly disulfide-linked, within the oligosaccharide side chain in the region preceding the first transmembrane domain ($N_39$).

On the basis of structural homologies with rhodopsin, it is likely that the amino terminus of the 5HT1c receptor is located on the extracellular side of the plasma membrane, with the carboxyl-terminus located intracellularly. In this scheme, three extracellular loops alternate with three intracellular loops to link the seven transmembrane domains.

Although the amino-terminal 65 amino acids of the 5HT1c receptor are thought to reside on the extracellular face of the membrane, the protein lacks a definable signal sequence. A potential N-linked glycosylation site is present at position 39. The receptor contains seven hydrophobic stretches (20 to 30 amino acids) that represent potential transmembrane domains. These domains constitute the regions of maximal sequence similarity with the other transmitter receptors of this class. The 5HT1c receptor shares 25% sequence identity with the $\beta_2$-adrenergic receptor, and 20% identity with the muscarinic and substance K receptors (FIG. 11).

A conserved aspartate residue is present within the second putative transmembrane domain and, by analogy with the $\beta_2$-adrenergic receptor, this residue may participate in ligand binding. Mutations in this conserved aspartate in the $\beta_2$-adrenergic receptor reduce agonist binding (52, 53). In addition, amino acid residues in this domain can be cross-linked to affinity ligands of the $\beta_2$-adrenergic receptor (50, 51). These data, taken together with the observation that all ligands capable of associating with this family of receptors have amino groups, suggest that aspartate participates in stabilizing the ligand in the plane of the membrane.

The third cytoplasmic loop, connecting transmembrane domains 5 and 6 and thought to interact with the different G proteins (54, 55, 56), is of widely varying length in different receptors. No sequence similarities within this domain are apparent among receptors that couple to common signaling systems. In the 5HT1c receptor, this loop consists of 77 amino acids, many of which are basic, a feature characteristic of other receptors in this family such as adrenergic and muscarinic receptors.

In the case of the serotonin receptor, lysine and arginine constitute 22% (17/77) of the total number of residues in this domain.

Both the carboxyl-terminal cytoplasmic domain and the third cytoplasmic loop contain sequences that may serve as substrates for phosphorylation by cyclic AMP-dependent protein kinase or protein kinase C. In addition, there are four serine residues in the carboxyl-terminal 12 amino acids which, by analogy with rhodopsin and the adrenergic receptors, may represent additional phosphorylation sites. These potential sites of phosphorylation may play a role in regulating the activity of the receptor molecule (57). Serine$_{312}$ in the variable loop lies within a consensus protein kinase C phosphorylation site, as does serine$_{382}$, located in the C-terminal tail.

Receptor expression in transfected mammalian cells

The deduced protein sequence of pSR-1c indicates that applicants have cloned a new member of the gene family encoding G-protein-coupled neurotransmitter receptors. To establish further that this clone encodes a serotonin receptor and to extend the ability to manipulate it, applicants have demonstrated that the introduction of this cDNA into mammalian fibroblasts renders these cells responsive to serotonin. The entire 3 kb EcoRI cDNA fragment from pSR-1c was subcloned into the expression vector pMV7 (58). This vector contains a murine leukemia virus long terminal repeat which serves as a promoter for expression of the serotonin cDNA as well as an independent expression cassette encoding neomycin phosphotransferase. Transformed NIH3T3 cells resistant to neomycin were isolated and a single clone expressing significant levels of receptor mRNA (SR3T3) was identified by RNA blot analysis.

Radioligand binding experiments were performed to determine whether SR3T3 cells display serotonin receptors on their surface. It has been previously shown that crude membranes prepared from the rat choroid plexus bind $^{125}$I-LSD specifically and with high affinity. Membranes prepared from SR3T3 cells exhibited high affinity binding sites for ligands that interact with the 5HT1c receptor on choroid plexus cells (3, 59). SR3T3 cells expressed $10^3$ to $10^4$ high affinity binding sites per cell for $^{125}$I-labeled lysergic acid diethylsites amide ($^{125}$I-LSD), whereas no specific high affinity sites were detected on the parental NIH3T3 cell line. Moreover, the relative ability of specific antagonists to inhibit $^{125}$I-LSD binding to SR3T3 cells paralleled their potency on choroid plexus cells (FIG. 12) (23). Mianserin ($IC_{50} = 20$ nM) was about two orders of magnitude more effective in displacing $^{125}$I-LSD binding than was spiperone ($IC_{50} = 2$ μM). Binding of $^{125}$I-LSD was also displaced by serotonin with an $IC_{50}$ value of 20 nM. The expression of specific high affinity binding sites for 5HT1c-selective ligands on transformed 3T3 cells provides independent confirmation that pSR-1c encodes a serotonin 1c receptor. Applicants conclude that the receptors expressed by SR3T3 cells are pharmacologically identical to those found in the choroid plexus.

Next, applicants determined whether serotonin can provoke the mobilization of intracellular calcium in transfected cells. This would provide a rapid and quantitative assay for ligand binding and transmembrane signaling.

To ascertain whether the binding of serotonin activates intracellular signaling pathways in transformed fibroblasts, SR3T3 cells were loaded with the $Ca^{2+}$-sensitive dye indo-1 and analyzed in a fluorescence-activated cell sorter (11). Indo-1 undergoes a characteristic and quantitative shift in its ratio of fluorescence emission at 400 and 500 nm wavelengths (excitation=360 nm) as a function of $Ca^{2+}$ concentration and serves (60). SR3T3 and control NIH3T3 cells loaded with indo-1 were exposed to serotonin immediately before fluorescence analysis to reduce the possibility of desensitization that may result from prolonged exposure of cells to agonist. In this way, all cells are examined at a fixed time following ligand-receptor interaction. Ninety-five percent of the SR3T3 cells loaded with indo-1 showed a marked increase in intracellular $Ca^{2+}$ when exposed to serotonin, whereas control, untransfected NIH3T3 cells did not respond to serotonin (FIG. 13) (Table I). SR3T3 cells sorted in the absence of serotonin also remain at low, resting calcium levels. These experiments indicate that the introduction of pSR-1c cDNA in mammalian fibroblasts leads to the expression of functional serotonin receptors. Thus the 5HT1c receptor is capable of triggering the same transduction machinery regardless of the cell type in which it is expressed.

TABLE I

| Immunoanalysis Results | | |
|---|---|---|
| MATCH RANGE | 13 | 41 |
| SUBTRACTION RANGE | 0 | 255 |
| PERCENT NEGATIVE | 5.7559 | |
| NUMBER | 1441. | |
| MEAN | 38.4607 | |
| STD DEVIATION | 33.4417 | |
| CV | 86.9503 | |
| SKEWNESS | 187.9516 | |

TABLE I-continued

Immunoanalysis Results

| | | |
|---|---|---|
| KURTOSIS | 0.0248 | |
| STATISTICS RANGE | 0 . . . | 255 |
| PERCENT POSITIVES | 94.244 | |
| NUMBER | 23561 | |
| MEAN | 135.798 | |
| STD DEVIATION | 27.5321 | |
| CT | 20.2743 | |
| SKEWNESS | 3.7435 | |
| KURTOSIS | 0.0003 | |
| STATISTICS RANGE | 41 . . . | 255 |

```
1 DJ      −25 15/1/88 20:48
1P256 3T3 PNV7K1 5 BL
RATIO    /RATIO,FALS
2 DJ      −15/1/88 20:57
1P256 3T3 PNV7K1 5 5HT
RATIO    /RATIO,FALS
```

Expression of 5HT1c serotonin receptor in the nervous system

RNA blot analysis and in situ hybridization (61) were performed to examine the expression of 5HT1c receptor mRNA in different brain regions and in peripheral tissues. Using a $^{35}$S-labeled anti-sense RNA probe for in situ hybridization, a heavy grain density associated with epithelial cells of the choroid plexus in the third, fourth and lateral ventricles was revealed. Strikingly, hybridization was not restricted to cells of the choroid plexus but appeared in numerous neuronal cell groups throughout the central nervous system. Labeled neurons were observed in the lateral habenula, whereas neurons in medial habenula were not labeled. Higher magnification of this region revealed the presence of silver grains in neuronal perikarya. The 5HT1c mRNA was also observed in neurons in cortical structures and in a variety of subcortical brain regions (62).

Filters to which poly A+ RNA from these tissues had been transferred were hybridized with a nick-translated probe prepared from the entire 3 kb EcoRI cDNA insert. A mouse alpha-actin probe was also used as an external calibration standard.

Although it is possible that the in situ analysis detects mRNA species other than that of the 5HT1c receptor, the distribution of 5HT1c receptor mRNA determined by in situ hybridization was supported by RNA blot analysis (FIGS. 14 and 15). An intense 5.2 kb RNA was observed in choroid plexus, and in a variety of other regions of the brain, including the basal ganglia, hypothalamus, hippocampus, pons medulla, and spinal cord. Longer exposure reveals the presence of a small amount of receptor mRNA in the olfactory bulb. Receptor RNA was not detected in the cerebellum or in liver, kidney, intestine, heart, and lung. Titration studies with purified pSR-1c RNA indicate that the 5HT1c receptor RNA comprises about 0.02% of the choroid plexus message population. The relative abundance of this RNA in other regions of the brain is at least ten times lower. In situ hybridization, however, indicated that some neurons express receptor mRNA levels comparable to those in choroid plexus cells. These findings demonstrate that the 5HT1c receptor is not restricted to epithelial cells of the choroid plexus, but is expressed in numerous discrete nueronal cell groups in many regions of the rat brain and spinal cord. This distribution of 5HT1c receptors suggests that this receptor subtype may mediate many of the central actions of serotonin.

Diversity of receptor subtypes

Applicants have cloned and characterized a functional cDNA encoding the 5HT1c subclass of serotonin receptor. RNA transcribed from this cDNA clone (pSR-1c) confers serotonin-sensitivity to Xenopus oocytes. The expression of pSR-1c in mouse fibroblasts results in the appearance of high affinity serotonin-binding sites on the cell surface. Exposure of these transformants to serotonin increases intracellular $Ca^{2+}$ levels. Moreover, abundant expression of 5HT1c receptor mRNA is observed in subsets of neurons throughout the brain, suggesting that the 5HT1c receptor plays an important role in central neurotransmission.

The procedure used to isolate the functional 5HT1c receptor cDNA has combined cloning in RNA expression vectors with a sensitive electrophysiological assay for serotonin receptor function in Xenopus oocytes. Similar procedures have been used to isolate the cDNA encoding the receptor for the neuropeptide substance K (30), and the $Na^+$-glucose cotransporter (63). The injection of as little as 5 pg of choroid plexus poly A+ RNA (1 fg of receptor mRNA) into oocytes was adequate to generate serotonin-evoked membrane currents. The sensitivity of the oocyte expression assay presumably results from the signal amplification associated with the coupling of these receptors to second messenger systems. In the oocyte, this assay is at present limited to receptors that activate second messenger systems, in particular phospholipase C, which elevates intracellular calcium levels. This cloning strategy may therefore be generally applicable to the isolation of genes encoding neurotransmitter and growth factor receptors that initiate a similar signal amplification, even if their mRNA's are present in exceedingly small amounts in the total RNA population.

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses. The variation in cellular response can be achieved by the association of individual receptor subtypes with different G proteins and different signaling systems. Further flexibility is provided by the ability of distinct receptors for the same ligand to activate or inhibit the same second messenger system. For example, among the adrenergic receptors, $\beta_1$ and $\beta_2$ receptors activate adenylate cyclase, $\alpha_2$ receptors inhibit adenylate cyclase and $\alpha_1$ receptors activate phospholipase C pathways (52, 53).

A similar array of cellular responses can be elicited by serotonin in cells bearing different receptor subtypes. Both 5HT1c and 5HT2 receptors stimulate the phospholipase C-mediated production of inositol phosphates, whereas 5HT1a and 5HT1b receptors may regulate adenylate cyclase activity (19, 20, 21) or couple to G proteins that directly activate ion channels (24, 25, 26, 27). The diverse neural actions of serotonin are thought to be mediated by activation of these distinct receptor subtypes. For example, the hallucinatory and perceptual disturbances associated with administration of LSD and other psychedelic serotonin analogs (67) are probably elicited by activation of cortical 5HT2 receptors (68). In contrast, the inflammatory and pain-producing effects of serotonin are mediated via 5HT3 receptors on peripheral sensory endings (69). The ability to express 5HT receptors in new cellular environments devoid of other receptor subtypes should permit the characterization of transduction systems associated with these specific receptors. Applicants anticipate that the cloning of additional receptor subtypes will help to elucidate the mechanisms of action of serotonin in the nervous system.

List of References Cited

1. Sanger, S., et al., Proc. Natl. Acad. Sci. USA 74: 5463-5467 (1987).
2. Maddon, P. J., et al., Cell 47: 333-348 (1986).
3. Yagaloff and Hartig, J. Neurosciences 5: 3178-3183 (1985).
4. Sumikawa, S., et al., Proc. Royal Soc. London, Series B 223: 255-260 (1984).
5. Gunderson, C., et al., Proc. Royal Soc. London, Series B 219: 103-109 (1983).
6. Lubbert, H., et al., J. Neurosciences 7: 1159-1165 (1987).
7. Cathala, G., et al., DNA 2: 329-335 (1983).
8. Krumlauf, et al., Development 99: 603-617 (1987).
9. Okayama, H. and Berg, P., Mol. Cell. Biol. 2: 161-170 (1982).
10. Wigler, et al., Cell 16: 777-785 (1979).
11. Schieren and MacDermott, J. Neurosci. Methods, in press.
12. Takaki, M., et al., J. Neurosciences 5: 1769 (1985).
13. Kravitz, E. A., et al., J. Exp. Biol. 89: 159 (1980).
14. Nemecek, G. M., et al., Proc. Natl. Acad. Sci. USA 83: 674 (1986).
15. Fields, H. L., in *Advances in Pain Research and Therapy*, L. Kruger and J. C. Liebeskind, Eds. (Raven Press, New York, 1984), Vol. 6, pp. 241-252.
16. White, S. R. and Neuman, R. S., Brain Res. 188: 119 (1980).
17. Jacobs, B. L., in *Hallucinogens: Neurochemical, Behavioral, and Clinical Perspectives*, B. L. Jacobs, Ed. (Raven Press, New York, 1984), pp. 183-202.
18. Peroutka, S. J., Ann. Rev. Neurosci. 11: 45 (1988).
19. DeVivo, M. and Maayani, S., J. Pharmacol. Exp. Ther. 238: 248 (1986).
20. Hoyer, D. and Schoekkter, P., Eur. J. Pharmacol. 147: 145 (1988).
21. Weiss, S., et al., Eur. J. Pharmacol. 120: 227 (1986).
22. de Courcelles, D., et al., J. Biol. Chem. 260: 7603 (1985).
23. Conn, P. J., et al., Proc. Natl. Acad. Sci. USA 83: 4086 (1986).
24. Aghajanian, G. K., in *Serotonin Neurotransmission and Behavior*, B. L. Jacobs and A. Gelperin, Eds. (MIT Press, Cambridge, Massachusetts, 1981), pp. 156-185.
25. Andrade, R., et al., Science 234: 1261 (1986).
26. Andrade, R. and Nicoll, R. A., J. Physiol. 394: 99 (1987).
27. Siegelbaum, S. A., et al., Nature 299: 413 (1982).
28. Takahashi, T., et al., Proc. Natl. Acad. Sci. USA 84: 5063 (1987).
29. Lubbert, H., et al., Proc. Natl. Acad. Sci. USA 84: 4332 (1987).
30. Masu, Y., et al., Nature 329: 836 (1987).
31. Pazos, A. and Palacios, J. M., Brain Res. 346: 205 (1985).
32. Stryer, L., in *Cold Sprinq Harbor Symp. Quant. Biol., Molecular Neurobiology* (Cold Spring Harbor Laboratory, Cold Spring Harbor, New York, 1983), Vol. 48, pp. 841-852.
33. Casey, P. J. and Gilman, A. G., J. Biol. Chem. 263: 2577 (1988).
34. Aviv, H. and Leder, P., Proc. Natl. Acad. Sci. USA 69: 1408 (1972).
35. Mayuhas, O. and Perry, R. P., Cell 16: 139 (1979).
36. Kraus, J. P., et al., Proc. Natl. Acad. Sci. USA 83: 2047 (1986).
37. Huynh, T. V., et al., in *DNA Cloning*, I.D.M. Glover, Ed. (RL Press, Oxford, 1985), Vol. 1, p. 49.
38. Watson, C. J. and Jackson, J. F., in *DNA Cloning*, I.D.M. Glover, Ed. (RL Press, Oxford, 1985), Vol. 1, p 79.
39. Sumikawa, K., et al., Proc. Natl. Acad. Sci. USA 81: 7994 (1984).
40. Maniatis, T., et al., in *Molecular Cloning* (Cold Spring Harbor Laboratory, Cold Spring Harbor, New York, 1982).
41. Nathans, J. and Hogness, D. S., Cell 34: 807 (1983).
42. Dohlman, H. G., et al., Biochemistry 26: 2657 (1987).
43. Bonner, T. I., et al., Science 237: 527 (1987).
44. Kubo, T., et al., Nature 323: 411 (1986).
45. Peralta, E., et al., Science 236: 600 (1987).
46. Burkholder, A. C. and Hartwell, L. H., Nucl. Acids Res. 13: 8463 (1985).
47. Hagan, D. C., et al., Proc. Natl. Acad. Sci. USA 83: 1418 (1986).
48. Nakayama, N., et al., EMBO J. 4: 2643 (1985).
49. Young, D., et al., Cell 45: 711 (1986).
50. Dohlman, H. G., et al., Biochemistry 27: 1813 (1988).
51. O'Dowd, B. F., et al., Ann. Rev. Neurosci., in press.
52. Chung, F.-Z., et al., J. Biol. Chem. 263: 4052 (1988).
53. Strader, C. D., et al., Proc. Natl. Acad. Sci. USA 84: 4384 (1987).
54. Dixon, R., et al., EMBO J. 6: 3269 (1987).
55. Strader, C. D., et al., J. Biol. Chem. 262: 16439 (1987a).
56. Dixon, R., et al., Nature 326: 73 (1987a).
57. Sibley, D. R., et al., Cell 48: 913 (1987).
58. Kirschmeir, P., et al., DNA, in press.
59. Kadan, M.J., et al., J. Neurochem. 43: 601 (1984).
60. Grynkiewicz, G., et al., J. Biol. Chem. 260: 3440 (1985).
61. Fremeau, R. T., et al., Science 234: 1265 (1986).
62. Molineaux, S., et al., in preparation.
63. Hediger, M. A., et al., Proc. Natl. Acad. Sci. USA 84: 2634 (1987).
64. Dixon, R., et al., Nature 321: 75 (1986).
65. Kobilka, B., et al., Science 238: 650 (1987).
66. Bonner, T. I., et al., Science 237: 527 (1987).
67. Leary, T., et al., in *The Psychedelic Experience* (University Books, New Hyde Park, New York, 1964).
68. Glennon, R. A., et al., Life Sci. 35: 2505 (1984).
69. Richardson, B. P., et al., Nature 316: 126 (1985).

What is claimed is:
1. An isolated DNA molecule encoding a serotonin 5HT1C receptor.
2. cDNA of claim 1.
3. A cDNA molecule of claim 2 comprising the nucleic acid sequence shown in FIG. 1.
4. A plasmid comprising the DNA of claim 1.
5. The plasmid of claim 4 designated pSR-1c and deposited under ATCC Accession No. 67636.

6. A plasmid adapted for expression in a mammalian cell which comprises the cDNA of claim 2 and the regulatory elements necessary for expression of the cDNA in the mammalian cell.

7. The plasmid of claim 6 designated pMV7-347.

8. A mammalian cell comprising the isolated DNA molecule of claim 1.

9. A mammalian cell comprising the cDNA of claim 2.

10. A mammalian cell comprising the plasmid of claim 6.

11. A transfected NIH3T3 cell comprising the plasmid of claim 7.

12. The transfected NIH3T3 cell designated SR3T3 and deposited under ATCC Accession No. CRL 9651.

13. A method for determining whether a ligand is capable in vivo of binding to the serotonin 5HT1c receptor which comprises contacting a mammalian cell of claim 10 with the ligand under conditions associated with in vivo binding of ligands to the serotonin 5HT1c receptor, detecting the presence of any of the ligand bound to the serotonin 5HT1c receptor and thereby determining whether the ligand binds to the serotonin 5HT1c receptor.

14. A method of claim 13, wherein the mammalian cell is SR3T3.

15. A method of detecting the expression of the serotonin 5HT1c receptor on the surface of a cell which comprises obtaining total mRNA from the cell and contacting the mRNA so obtained with the cDNA of claim 2 under hybridizing conditions, detecting the presence of mRNA hybridized to the cDNA, and thereby detecting the expression of the serotonin 5HT1c receptor by the cell.

16. A DNA probe useful for detecting nucleic acid encoding the serotonin 5HT1c receptor comprising a nucleic acid molecule of at least about 13 nucleotides having a sequence complementary to a sequence included within the sequence shown in FIG. 1.

17. A method of screening drugs to identify drugs which specifically interact with, and bind to, the serotonin 5HT1c receptor on the surface of a cell which comprises contacting the mammalian cell of claim 10 with a plurality of drugs, determining those drugs which bind to the mammalian cell, and thereby identify drugs which specifically interact with, and bind to, the serotonin 5HT1c receptor.

* * * * *